(12) United States Patent
Yang et al.

(10) Patent No.: US 6,867,166 B2
(45) Date of Patent: Mar. 15, 2005

(54) SELECTIVE ADSORPTION OF ALKENES USING SUPPORTED METAL COMPOUNDS

(75) Inventors: Ralph T. Yang, Ann Arbor, MI (US); Joel Padin, Ann Arbor, MI (US); Salil U. Rege, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 10/082,550

(22) Filed: Feb. 25, 2002

(65) Prior Publication Data

US 2003/0060360 A1 Mar. 27, 2003

Related U.S. Application Data

(62) Division of application No. 09/177,256, filed on Oct. 22, 1998, now Pat. No. 6,423,881.

(51) Int. Cl.$^7$ ................................................ B01J 20/22
(52) U.S. Cl. ........................................................ 502/401
(58) Field of Search ................................ 502/401, 407, 502/417, 74, 66, 68, 84

(56) References Cited

U.S. PATENT DOCUMENTS

| | | | |
|---|---|---|---|
| 2,685,607 A | | 8/1954 | Pevere et al. |
| 2,882,243 A | | 4/1959 | Milton |
| 2,882,244 A | | 4/1959 | Milton |
| 3,130,007 A | | 4/1964 | Breck |
| 3,243,471 A | | 3/1966 | Stem |
| 3,669,903 A | * | 6/1972 | Bourguet et al. ............. 502/74 |
| 3,785,122 A | | 1/1974 | Yatsurugi et al. |
| 3,992,471 A | | 11/1976 | Priegnitz |
| 4,019,880 A | | 4/1977 | Rabo et al. |
| 4,341,664 A | * | 7/1982 | Antos ........................ 502/327 |
| 4,659,477 A | * | 4/1987 | Macedo et al. ............. 588/248 |
| 4,717,398 A | | 1/1988 | Pearce |
| 4,917,711 A | | 4/1990 | Xie et al. |
| 5,268,023 A | | 12/1993 | Kirner |
| 5,365,011 A | | 11/1994 | Ramachandran et al. |
| 5,551,257 A | | 9/1996 | Jain |
| 5,554,208 A | | 9/1996 | Mullhaupt et al. |
| 5,656,064 A | | 8/1997 | Golden et al. |
| 5,672,196 A | | 9/1997 | Acharya et al. |
| 5,675,052 A | | 10/1997 | Menon et al. |
| 5,713,984 A | | 2/1998 | Monnot et al. |
| 5,744,687 A | | 4/1998 | Ramachandran et al. |
| 6,074,973 A | * | 6/2000 | Lampert et al. .............. 502/60 |

OTHER PUBLICATIONS

"Olefin/Paraffin Separations by Adsorption: π—Complexation vs. Kinetic Separation" Salil U. Rege, Joel Padin, and Ralph T. Yang, AIChE Journal, Apr. 1998, vol. 44, No. 4, pp. 799–809.

"*Separations* Modification of Resin-Type Adsorbents for Ethane/Ethylene Separation," Zhongbiao Wu, Sang–Sup, Han, Soon–Haeng Cho, Jong–Nam Kim, Kuck–Tack Chue, and Ralph T. Yang. Ind. Eng. Chem. Res. 1997, 36, 2749–2756. no month.

"Gas Separation and Purification by Polymeric Adsorbents: Flue Gas Desulfurization and $So_2$ Recovery with Styrenic Polymers", E.S. Kikkinides and R.T. Yang, Ind. Eng. Chem. Res. 1993, 32, 2365–2372. no month.

"*Materials and Interfaces*" Ab Initio Molecular Orbital Study of Adsorption of Oxygen, Nitrogen, and Ethylene on Silver–Zeolite and Silver Halides:, N. Chen and R.T. Yang, Ind. Eng. Chem. Res. 1996, 35, 4020–4027. no month.

New Sorbents for Olefin/Paraffin Separations by Adsorption via π—Complexation, R. T. Yang and E. S. Kikkinides, AlChE Journal, Mar. 1995, Vo. 41, No. 3, pp. 509–517.

"Spontaneous Monolayer Dispersion of Oxides and Salts onto Surfaces of Supports: Applications to Heterogeneous Catalysts," You–Chang Xie and You–Qi Tang, Advances in Catalysis, vol. 37, pp. 1–43, no date.

* cited by examiner

*Primary Examiner*—Stanley S. Silverman
*Assistant Examiner*—Edward M. Johnson
(74) *Attorney, Agent, or Firm*—Dierker and Associates, P.C.

(57) ABSTRACT

The invention provides novel adsorbents for use in the separation of unsaturated hydrocarbons from a mixture of gases containing such hydrocarbons. The preferred adsorbents comprise metal compounds supported on high surface area carriers. The adsorbents of the invention are usable in pressure swing adsorption or temperature swing adsorption processes.

17 Claims, 11 Drawing Sheets

SELECTIVE ADSORPTION OF ALKENES USING SUPPORTED METAL COMPOUNDS

CROSS-REFERENCE TO RELATED APPLICATIONS

This application is a divisional of U.S. application Ser. No. 09/177,256, filed Oct. 22, 1998, now U.S. Pat. No. 6,423,881.

STATEMENT OF GOVERNMENT SUPPORT

This invention was made with government support provided by the National Science Foundation under the terms of Contract No. CTS-9520328. The government has certain rights in the invention.

BACKGROUND OF THE INVENTION

The present invention relates to a process and new sorbents for selective adsorption and recovery of alkenes from gaseous mixtures containing the alkenes.

Several methods are known for the separation of selected organics from gaseous mixtures. These include, for example, cryogenic distillation, liquid adsorption, membrane separation and pressure swing adsorption in which adsorption occurs at a higher pressure than the pressure at which the adsorbent is regenerated. In an analogous method, temperature swing adsorption is used in which adsorption occurs at a lower temperature than the temperature at which the adsorbent is regenerated. In these adsorption techniques, after adsorption occurs, release of the adsorbed material is achieved by either decreasing the pressure or raising the temperature. Of these methods, cryogenic distillation and liquid adsorption represent commonly known methods for separating selected organics from gaseous mixtures. Cryogenic distillation has been used for over sixty years for separation. However, it is very energy intensive and difficult to accomplish because of relatively close volatilities when alkene\alkane (olefin\paraffin) separation is required. For example, ethane\ethylene separation is carried out at about −25° C. and 320 psig (2.603 MPa) in a column containing over 100 trays, and propane\propylene separation is performed by an equally energy-intensive distillation at about −30° C. and 30 psig (0.308 MPa). It is evident that high capital costs and high operational costs are incurred in any cryogenic distillation approach. Early attempts were made to use liquid solutions for separation by means of metallic ions dispersed in solution. Such methods are very difficult to conduct and not easily adaptable to commercial use.

More recently, molecular sieve zeolites have been investigated to selectively adsorb carbon monoxide and hydrocarbons from gaseous mixtures. However, these zeolites have shown only moderate capacity for recovery of the targeted compound to be adsorbed. An example is adsorption on cuprous ion exchange y-type zeolites (U.S. Pat. Nos. 4,717,398 and 5,365,011). Presently, many of the available adsorbents known for other uses, such as carbon monoxide removal, do not have selectivities for olefins as demonstrated by the aforesaid '398 and '011. Therefore, what is needed are new adsorbents (sorbents) effective for olefin/paraffin separation.

SUMMARY OF THE INVENTION

The invention provides new adsorbents for use in separating selected gaseous hydrocarbons from a mixture comprising the hydrocarbons. The invention provides new methods for accomplishing such separation using the novel adsorbents. The new adsorbents are very effective for selective adsorption of alkenes such as ethylene, propylene, and mixtures of these from a gaseous mixture which comprises the alkene. In one embodiment, the invention provides an adsorbent for preferential adsorption which comprises a metal compound supported on a carrier. The metal compound is characterized by the ability to releasibly retain the alkene whereby the alkene is preferentially adsorbed from the mixture. This produces a non-adsorbed component and an alkene-rich adsorbed component. Next, by changing at least one of pressure and temperature, the alkene-rich component is thereby released from the adsorbent.

The adsorbent preferably comprises a metal compound selected from a silver compound, a copper compound and mixtures thereof. The preferred carrier comprises a plurality of pores having size greater than the molecular diameter of the alkene. The compound of silver or copper is characterized by formation of π-complexation bonds between the silver or copper and the alkene for accomplishing the retention of the alkene by the adsorbent. When pressure and/or temperature is changed, the silver or copper compound releases the alkene-rich component from the adsorbent.

The metal compound is preferably a salt selected from acetate, benzoate, bromate, chlorate, perchlorate, chlorite, citrate, nitrate, nitrite, sulfate and halide (F, Cl, Br, I) and mixtures of these. The preferred silver salt is silver nitrate. Other salts of silver are as per the group defined above where the preferred halide is fluoride. Another preferred adsorbent is salt of copper selected from the group consisting of bromide, fluoride, iodide and sulfates, supported on a carrier.

The carrier is a high surface area support selected from refractory inorganic oxide, molecular sieve, activated carbon, pillared clay, and mixtures of these. The carriers are preferably characterized by a BET surface area greater than about 50 square meters per gram and up to about 2,000 square meters per gram and comprise a plurality of pores having size greater than about 3 angstroms and up to about 10 microns. Preferably, the adsorbent comprises finely divided particles of silica with silver nitrate dispersed on and supported on the particles.

Preferential adsorption is achieved at a pressure greater than the desorption (release) pressure. Preferential adsorption pressure may be as high as about 35 atmospheres or more; and the desorption pressure may be as low as subatmospheric, significant vacuum, 0.01 atmosphere or less. The pressure of preferential adsorption is in a range of about 1 to about 35 atmospheres; desirably about 1 to 10 atmospheres; and most desirably about 1 to about 2 atmospheres. The pressure of release is in a range of about 0.01 atmospheres to about 5 atmospheres; and desirably in a range of about 0.1 atmospheres to about 0.5 atmospheres.

The temperature of preferential adsorption is conveniently selected to be in a range of about 0° C. to about 50° C.; and desirably in a range of about 25° C. to about 50° C. The temperature of release is selected to be in a range of about 70° C. to about 200° C.; and desirably 100° C. to about 120° C.

There are several methods for accomplishing dispersion of the metal compound onto a carrier or support. These methods include thermal monolayer dispersion, impregnation by incipient wetness technique, and spray application. In a preferred embodiment, the adsorbent of the invention is prepared by dispersing the metal compound onto the carrier under conditions that do not decompose or oxidize the compound. It is preferred that the dispersion permits the chemical compound to retain its character. The impregnation by incipient wetness technique accomplishes these objectives. This technique avoids decomposition of the metal compound which is more likely to occur by thermal dispersion heating method. Further, incipient wetness technique permits the defective dispersion of a monomolecular layer of metal compound on the carrier.

The invention provides substantial advantages over conventional methods for separating components of a gaseous mixture due to the effective and economical process and adsorbents provided by the invention.

It would be desirable to provide an improved method for separating olefins from paraffins. It would further be desirable to provide new adsorbents for use in such separation.

BRIEF DESCRIPTION OF THE DRAWINGS

Objects, features and advantages of the present invention will become apparent by reference to the following detailed description and drawings, in which.

DETAILED DESCRIPTION OF THE PREFERRED EMBODIMENTS

Figure 1:
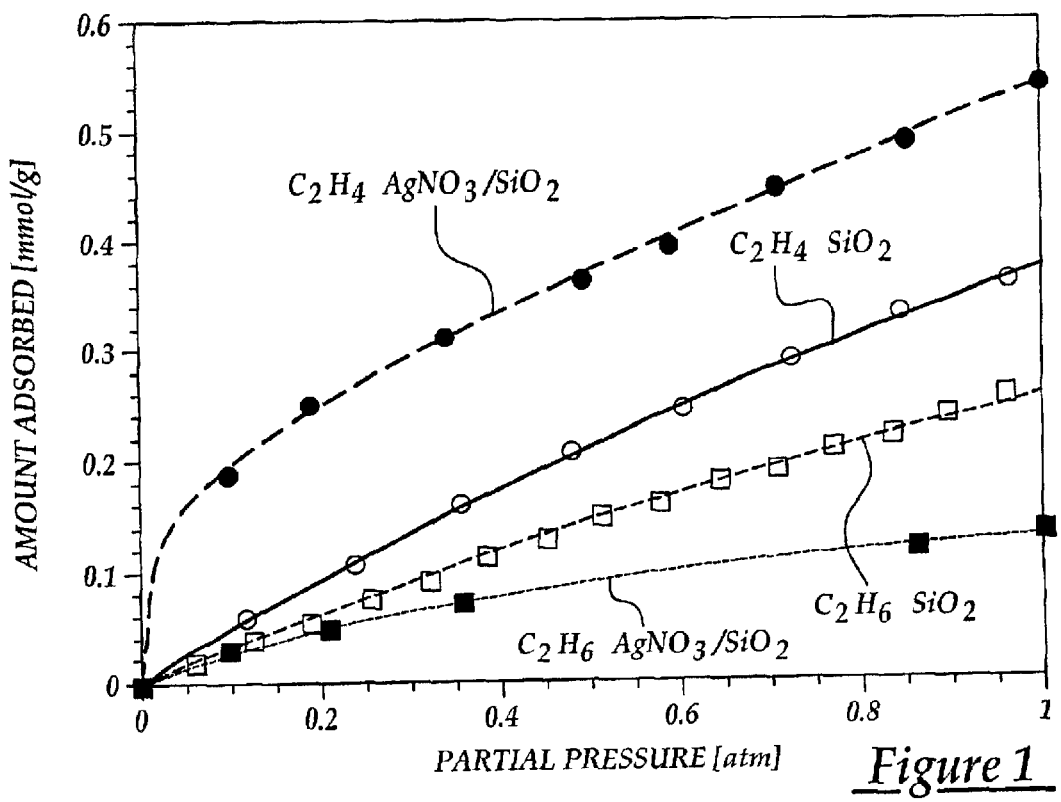
FIG. 1 shows equilibrium isotherms of $C_2H_4$ and $C_2H_6$ at 70° C. on $SiO_2$ and $AgNO_3/SiO_2$ prepared via thermal monolayer (monomolecular layer) dispersion method at 70° C. Lines are fittings with eqs. (A) and (B).

The invention provides novel adsorbents for use in a method of separating selected gaseous hydrocarbons from a gaseous mixture comprising such hydrocarbons. The adsorbents are particularly suited for selective adsorption of alkenes such as ethylene, propylene, and mixtures of these from a gaseous mixture comprising alkenes. In one embodiment, the method comprises first contacting the gaseous mixture with an adsorbent comprising a metal compound which preferentially adsorbs the alkene, at a selected temperature and pressure, thereby producing a non-adsorbed component and an alkene-rich adsorbed component. The adsorbent comprises a metal compound, preferably a silver or copper compound supported on a carrier. The preferred carrier comprises a plurality of pores having size greater than the effective molecular diameter of the alkene. The compound of silver or copper is characterized by formation of π-complexation bonds between the silver or copper and the alkene for releasably retaining the alkene. Then the pressure and/or temperature are changed to thereby release the alkene-rich component from the adsorbent.

The metal compound is preferably a salt selected from acetate, benzoate, bromate, chlorate, perchlorate, chlorite, citrate, nitrate, nitrite, sulfate, halide (FE, Cl, Br, I), and mixtures of these. The carrier is a high surface area support selected from refractory inorganic oxide, molecular sieve, and activated carbon, and mixtures of these. The preferred metal is selected from silver and copper, and mixtures thereof In one embodiment, the adsorbent is characterized by preferential adsorption of gaseous alkene from a gaseous mixture comprising the alkene, and the adsorbent comprises a salt of silver supported on a carrier. The preferred salt is silver nitrate. Other salts of silver are as per the group defined above, where the preferred halide is fluoride.

Preferably, the adsorbent comprises finely divided particles of silica ($SiO_2$) with silver nitrate dispersed on and supported on the particles.

Another preferred adsorbent is a salt of copper selected from the group consisting of bromide, fluoride, iodide and sulfate, supported on a carrier.

The carriers are refractory inorganic oxide, molecular sieve, and activated carbon. The carriers are preferably characterized by a BET surface area greater than about 50 square meters per gram and up to about 2,000 square meters per gram and comprise a plurality of pores having size greater than about 3 angstroms and up to about 10 microns.

In a preferred embodiment, the metal compound retains its chemical characteristic. Therefore, dispersion onto a carrier is preferably conducted under conditions that do not decompose or oxidize the metal compound. In addition, the preferred metal compound is one that provides the metal in a +1 oxidation state. The preferred dispersion method leads to such preferred +1 valance state. Preferably, the metal compound is water soluble to facilitate dispersion, particularly by incipient wetness technique. Therefore, the preferred compound contains Ag(I) or Cu(I) cationic species with associated anionic species, as per the compound and salts listed above. As a result, these n-complexation adsorbents of the invention provide attractive and improved results compared to conventional adsorbents.

Separation by π-complexation is a subgroup of chemical complexation where the mixture is contacted with a second phase, which contains a complexing agent. The advantage of chemical complexation is that the bonds formed are stronger than those by van der Waals forces alone, so it is possible to achieve high selectivity and high capacity for the component to be bound. At the same time, the bonds are still weak enough to be broken by using simple engineering operations such as raising the temperature or decreasing the pressure.

The π-complexation generally pertains to the main group (or d-block) transition metals, that is, from Sc to Cu, Y to Ag, and La to Au in the periodic table. These metals or their ions can form the normal a bond to carbon and, in addition, the unique characteristics of the d orbitals in these metals or ions can form bonds with the unsaturated hydrocarbons (olefins) in a nonclassic manner. This type of bonding is broadly referred to as π-complexation, and has been considered for gaseous hydrocarbon separation and purification using cumbersome liquid solutions.

The further description and examples below show that for $C_3H_6/C_3H_8$ separation, conventional sorbents did not provide a large working capacity for $C_3H_6$ since the $C_3H_6$ isotherms do not exhibit a steep portion between adsorption and desorption pressures. The examples also show that the sorbents of the invention have superior selectivity for $C_3H_6$ adsorption. The examples show use of the new adsorbents (sorbents) with a preferred PSA process for very effective gas separation.

The PSA process is effectively usable with the new sorbents of the invention. Here, multiplicity of periodic steady states is an important aspect of cyclic adsorption process. For pressure swing adsorption (PSA), multiple steady states exist for a fixed set of operating conditions, over a particular range of one or more of these operating variables (i.e., bifurcation variables). The final stable state depends only on the initial condition (i.e., the perturbation variables). Such an example of multiplicity in PSA has been presented for the system of $H_2S/CO_2/CH_4$ on 5A zeolite. Efficient methods for direct determination of periodic steady states as well as mapping regions with different bifurcation diagrams are applied to PSA. Here, there is used a region of multiplicity for $C_3H_6/C_3H_8$ separation by PSA coupled with the new sorbents.

To further illustrate the present invention, the following examples are given. It is to be understood that these examples are provided for illustrative purposes and are not to be construed as limiting the scope of the present invention.

EXAMPLE 1

$AgNO_3$ Supported on $SiO_2$ Prepared by Thermal Monolayer Dispersion and Incipient Wetness Impregnation The sorbents of the invention are metal compounds which contain metal cations dispersed over a high surface area substrate. The dispersion of metal compounds and their included cations was accomplished using several methods. This was done to determine which technique was better suited for preparing π-complexation sorbents. One of the methods is known as spontaneous thermal monolayer dispersion. The other technique utilized was incipient wetness impregnation. Here, these techniques were applied to synthesize sorbents capable of π-complexation with olefins.

Thermal monolayer dispersion involves mixing a metal compound, preferably a metal salt, with a substrate at a predetermined ratio. This ratio is determined by the amount of salt that is required for monolayer coverage on the surface area of the substrate assuming two-dimensional close-packing. The BET surface area of the substrate was first measured. After the finely divided powders of the salt and substrate have been thoroughly mixed, it was heated at a temperature between the Tammann temperature and the melting point of the salt. If the temperature was too low, the dispersion would take an unacceptably long time. However, a high dispersion temperature could cause the metal salt to oxidize or react with the substrate, both of which could deactivate the sorbent. The sorbent in the example was prepared by mixing 0.32 grams of $AgNO_3$ (Strem Chemicals) per gram of $SiO_2$ (Strem Chemicals). After thorough mixing, the sample was heated in air at 200° C. for 89 hours to assure complete dispersion. This sorbent is referred to as monolayer $AgNO_3/SiO_2$. The BET surface area of this sample was measured at 384 $m^2/g$. The above ratio yielded the best results for this dispersion technique.

Another technique utilized was incipient wetness impregnation. It involved preparing a solution of the salt to be dispersed. The solution was then mixed with the substrate where it was absorbed by the substrate due to incipient wetness. After the substrate had imbibed the solution containing the salt into its pore structure, the sample was heated to remove the solvent. Care needs to be taken when selecting solvents for use in this technique. Firstly, the salt needs to be soluble in the solvent to a sufficient extent so as to allow enough salt to be dissolved in the volume of solution that is equal to the pore volume of the substrate. Secondly, the solvent selected needs to be able to wet the surface of the substrate. As mentioned above, $AgNO_3/SiO_2$ at a ratio of 0.32 was the sorbent utilized. Since $AgNO_3$ is highly soluble in water, water was chosen as the solvent. Also, since $SiO_2$ has a high affinity for water, this also assures proper wetting of the substrate. The pore volume and surface area of the $SiO_2$ utilized were measured at 0.46 $cm^3/g$ and 670 $m^2/g$, respectively. A 1.2 M solution of $AgNO_3$ was prepared. A volume of the solution equal to the total pore volume of $SiO_2$ sample was brought in contact with the substrate, so that an $AgNO_3/SiO_2$ ratio equal or close to 0.32 was achieved. The sample was then heated for 4 hours at 105 °C. in air to remove the water. The ratio of the resulting sample was calculated at 0.27 and the sample was used without further treatment. The BET surface area of this sorbent was 398 $m^2/g$. The sorbent prepared by incipient wetness impregnation is referred to as impregnated $AgNO_3/SiO_2$. The loadings of $AgNO_3$ on the samples were optimized by maximizing olefin adsorption while varying the salt content.

Adsorbates

The hydrocarbons used as the adsorbates were ethane (CP grade, Matheson minimum purity 99.0%), ethylene (CP grade, Matheson minimum purity 99.5%), propane (CP grade, Matheson minimum purity 99.0%), and propylene (CP grade, Matheson minimum purity 99.0%). Helium (pre-purifed grade, Metro Welding 99.995%) was used as the carrier gas and as the regeneration gas. The gases were used without further purification.

Measurements of Equilibrium Isotherms and Uptake Rates

Isotherms and uptake rates were measured utilizing both a Shimadzu TGA-50 microbalance and a Micromeritics ASAP 2010 system following the procedures described in Ackley and Yang (1991). Equilibrium time for isotherm measurements was about 5 minutes per equilibration point. Surface area measurements were made using the Micromeritics ASAP 2010. Also, measurements were made at two temperatures (25° C., 70° C.) in order to obtain isosteric heats of adsorption. The overall diffusion time constants, $D/R^2$, were calculated from the uptake curves measured from a stepped pressure increment from 0 to 0.1 atm by methods and assumptions described in detail in Yeh (1989).

Equilibrium Isotherm Model

Since the adsorption of paraffin molecules includes physical adsorption only, it can be modeled well by the Langmuir isotherm with two parameters shown in equation A.

However, the adsorption of olefin molecules on $AgNO_3/SiO_2$ includes both physical adsorption and chemisorption (via π-complexation). Therefore, a different model is required to account for chemisorption. The isotherm model developed by Yang and Kikkinides (1995) to account for both interactions is shown in equation B.

The first term accounts for physical adsorption, while the second term represents contributions by chemisorption. The second term also takes into account the energetic heterogeneity of the surface ion sites available for complexation. While equation B contains five parameters, only two of them are true fitting parameters (Yang and Kikkinides, 1995). The other three parameters have certain constraints imposed on them in order for them to have physical meaning. Empirical values for s are available from the literature (Valenzuela and Myers, 1989; Kapoor and Yang, 1990). For each adsorbent, the corresponding paraffin data were used first to obtain the two parameters in the Langmuir isotherm. Therefore, equation B was used to fit the olefin adsorption data with imposed values or constraints on $q_{mp}$ and $b_p$, and s, leaving only $q_{mc}$ and $b_c$ as true fitting parameters.

Thermal Monolayer Dispersion vs. Incipient Wetness Impregnation for Preparing $AgNO_3$ Supported on $SiO_2$ As mentioned earlier, the thermal dispersion involves heating a mixture of metal salt and substrate. This could lead to oxidation or partial oxidation of the metal salt, which would reduce the complexation with olefin molecules. It was determined that $FeCl_2$ could be easily oxidized to $FeCl_3$ during the thermal monolayer dispersion process. As also described earlier, metal cations can be spread by incipient wetness impregnation. Sorbents prepared by these two techniques are compared in this example. It should be noted that thermal monolayer dispersion (TMD) is also referred to as thermal dispersion. These terms are used interchangeably throughout this description. It should be noted that the incipient wetness impregnation method also results in the creation of a monomolecular layer or monolayer of the salt dispersed on the carrier or support. Therefore, as used herein, impregnation refers to the monolayer achieved by the more superior incipient wetness method and thermal dispersion generally refers to application of the salt onto an adsorbent by high temperature thermal processing.

$AgNO_3/SiO_2$ sorbent capable of π-complexation was prepared via thermal monolayer dispersion. The procedure for the preparation of the sorbent was described in the previous section, including that the process was carried out at 200° C. for 89 hours in order to allow sufficient time for the dispersion of the $AgNO_3$ salt. The resulting sorbent had a light gray color which suggested that some of the $AgNO_3$ had been oxidized during the process. The BET surface area of the sorbent was measured at 384 $m^2/g$. The average pore diameter of the sorbent was calculated using the Horvath-Kawazoe method to be 8.4 Å.

Equilibrium isotherms of $C_2H_4$ and $C_2H_6$ on $SiO_2$ (substrate) and monolayer $AgNO_3/SiO_2$ (by thermal dispersion) at 70° C. are shown in FIG. 1. The equilibrium data for $C_2H_6$ and $C_2H_4$ were fitted to equations A and B, respectively. Fitting parameters for these isotherms are shown in Table A. Although both gases adsorbed similar amounts on the $SiO_2$ surface, the adsorbed amount of $C_2H_4$ was slightly higher than that for $C_2H_6$. From FIG. 1, it can be seen that the bare surface of $SiO_2$ showed no substantial selectivity. The selective adsorption ratio of $C_2H_4$ over $C_2H_6$ for $SiO_2$ was approximately 1.5. The preference toward $C_2H_4$ is due to higher polarizability. This allows $C_2H_4$ to better interact with the electric field on the surface of the $SiO_2$ substrate. Compared to $SiO_2$, monolayer $AgNO_3/SiO_2$ demonstrated a substantial increase in selectivity and capacity for olefin. The selective adsorption ratio of $C_2H_4$ over $C_2H_6$ was increased from 1.5 to 4. On monolayer $AgNO_3/SiO_2$ at 70° C. and 1 atm, the amount adsorbed for $C_2H_4$ was 0.5 mmol/g. It appears that the increase in $C_2H_4$ adsorption on monolayer $AgNO_3/SiO_2$ was not large when compared to adsorption on bare $SiO_2$. However, it becomes more significant when one compares the amounts adsorbed per surface area. The amount of $C_2H_4$ absorbed per surface area increased two fold on $AgNO_3/SiO_2$.

Figure 2:
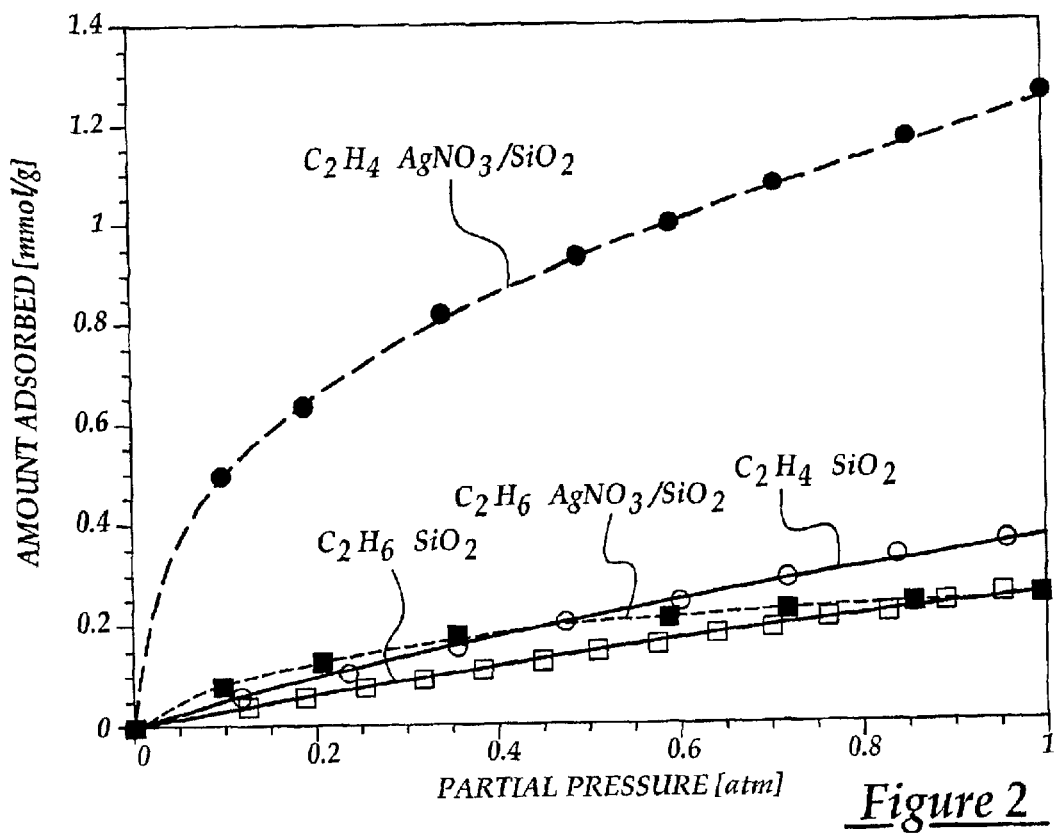
FIG. 2 shows equilibrium isotherms of $C_2H_4$ and $C_2H_6$ at 70° C. on $AgNO_3/SiO_2$ prepared via incipient wetness impregnation method. Lines are fittings with eqs. (A) and (B).

In order to compare thermal monolayer dispersion with incipient wetness impregnation, equilibrium isotherms for $C_2H_4$ and $C_2H_6$ at 70° C. on wet impregnated $AgNO_3/SiO_2$ are shown in FIG. 2. The equilibrium data for $C_2H_6$ and $C_2H_4$ was fitted with equations A and B, respectively. The fitting parameters are shown in Table A. When compared with the sorbent synthesized by thermal monolayer dispersion, this sorbent showed superior capacity and a higher selectivity. At 1 atm and 70° C., on impregnated $AgNO_3/SiO_2$, the amount adsorbed of $C_2H_4$ was 1.25 mmol/g. The capacity of this sample was 2.5 times greater than that on the same sorbent prepared by thermal monolayer dispersion. The selective adsorption ratio was 6.5. This was approximately a 60% increase over monolayer $AgNO_3/SiO_2$. Both sorbents demonstrated completely reversible adsorption behavior.

Figure 2A:
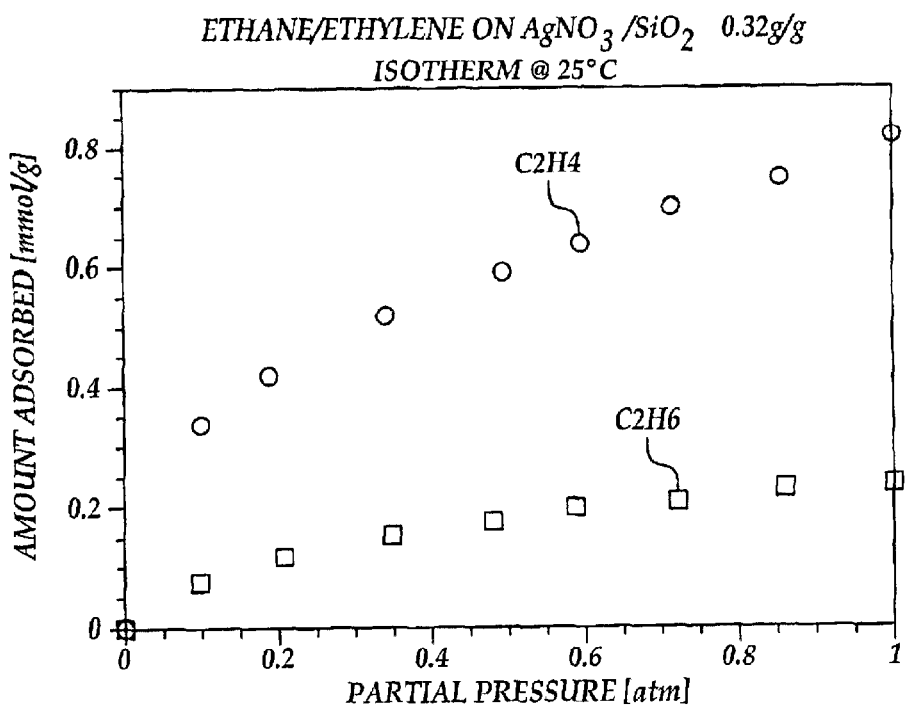
FIG. 2A shows equilibrium isotherms of $C_2H_4$ and $C_2H_6$ at 25° C. on $AgNO_3/SiO_2$ sorbent. This sorbent was prepared by impregnating $SiO_2$ with the $AgNO_3$, using incipient wetness technique to achieve a monomolecular layer of the Ag salt on the $SiO_2$ carrier.

FIG. 2A shows equilibrium isotherms of $C_2H_4$ and $C_2H_6$ at 25° C. on $AgNO_3/SiO_2$ sorbent. This sorbent was prepared by impregnating $SiO_2$ with the $AgNO_3$, using incipient wetness technique to achieve a monomolecular layer of the Ag salt on the $SiO_2$ carrier. Comparing FIGS. 1 and 2A, there is shown significant improved performance of the impregnated (incipient wetness prepared) $AgNO_3$ on $SiO_2$ sorbent as compared to the thermally dispersed $AgNO_3$ on $SiO_2$. The impregnated sorbent (FIG. 2A) has a shape of the isotherm that is higher above the knee. This isotherm shape is desirable because it increases the working capacity of the sorbent. Comparing FIGS. 1 (thermally dispersed) and 2A (impregnated) it is clear that the impregnated sorbents are superior.

The enhanced performance of the impregnated sorbents (FIGS. 2 and 2A) over the thermally dispersed sorbents (FIG. 1) is clear. The amounts of $C_2H_4$ adsorbed in FIGS. 2 and 2A are far greater at each partial pressure than the amount adsorbed in FIG. 1 at the same respective partial pressure.

One possible explanation for the increased adsorption capacity of the sorbent prepared via wet impregnation was better salt dispersion and hence less pore blockage. However, when the surface areas were compared (380 vs. 389 $m^2/g$), no significant differences were encountered. Also, the fact that diffusion in both samples was fast indicated no or minimal pore blockage. Complete diffusional uptake was achieved in less than 90 seconds for both sorbents. Another possible explanation was the $AgNO_3$ loading on the sample. Again when both loadings were compared (0.32 vs. 0.27), no significant difference was encountered that accounts for the large difference on adsorption capacities. Lastly, the only plausible explanation for the discrepancies was the nature or oxidation states of the dispersed cations. As mentioned, thermal monolayer dispersion could lead to partial oxidation of the salt. Since $AgNO_3$ was exposed to air at 200° C. for 89 hours during thermal monolayer dispersion, it is possible that some of the salt was oxidized to some extent. A simple evidence for partial oxidation and decomposition was the observation of the color of the resulting sample which had a light gray color with some black particles. This observation indicated that some of the $AgNO_3$ salt (which is colorless) was decomposed and oxidized to $Ag_2O$ and AgO (gray and black, respectively). The decomposition/partial oxidation of some of the $AgNO_3$ would certainly decrease the complexation with olefin and hence the adsorption capacity.

EXAMPLE 2
Anion Effects—Ag-Halide Compounds Supported on $SiO_2$

In this example, the effect of various anions on olefin adsorption is shown. By understanding this effect, the adsorptive properties of sorbents are maximized for olefin/paraffin separation. The sorbents were prepared by dispersing silver halides on silica gel via thermal monolayer dispersion. Incipient wetness impregnation was not used due to lack of good solvents. The halides used were AgF, AgCl, AgBr, and AgI. The silver halide content of each sorbent was maintained at around 1.0 mmol/g to facilitate comparison. The sorbents were prepared by mixing the metal halide and the silica gel with thorough mixing. The resulting mixture was heated in air at 350° C. for 4 days to assure proper spreading. The BET surface areas of the resulting sorbents are shown in Table B.

Figure 3:
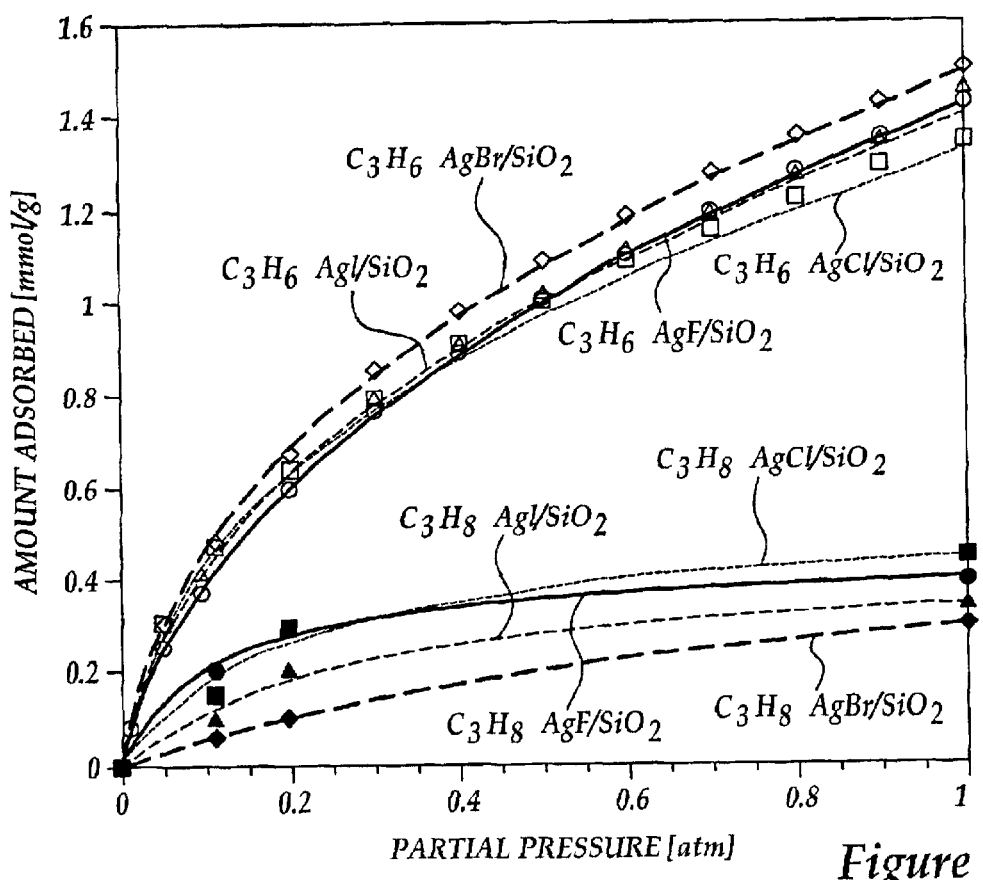
FIG. 3 shows equilibrium isotherms of $C_3H_6$ at 25° C. on $AgX/SiO_2$ via thermal monolayer dispersion method.
Figure 4:
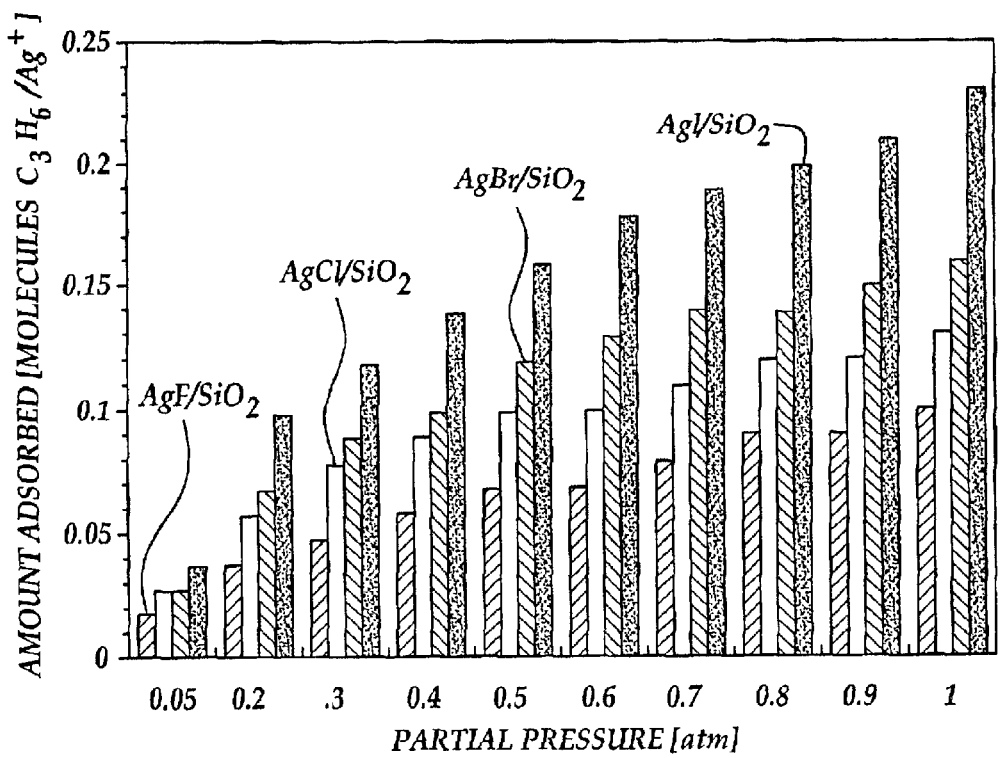
FIG. 4 shows normalized $C_3H_6$ equilibrium data at 25° C. on $AgX/SiO_2$ via thermal monolayer dispersion method.

Equilibrium isotherms for $C_3H_6$ at 25° C. on the various $AgX/SiO_2$ (where X=F, Cl, Br, or I) sorbents are shown in FIG. 3. The fitting parameters for these isotherms are shown in Table C. The amounts of $C_3H_6$ adsorbed at 1 atm for AgF, AgCl, AgBr and AgI on $SiO_2$ were 1.44, 1.34, 1.51, and 1.47 mmol/g, respectively. All isotherms were fully reversible. Initially, it would appear that anions have very slight effect. However, when the data are normalized to account for differences in surface area, a clear trend emerged. The normalized data are shown in FIG. 4. The weakly chemisorbed $C_3H_6$ on the surface metal cations can be represented by the following formula: $Ag^+(C_3H_6)_n$. The values of n for $AgF/SiO_2$, $AgCl/SiO_2$, $AgBr/SiO_2$, $AgI/SiO_2$ at 1 atm and 25° C. were 0.10, 0.13, 0.16 and 0.23 molecule $C_3H_6$ per $Ag^+$. Therefore, once the data was normalized, the adsorption trend was observed as follows:

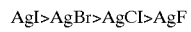

AgI>AgBr>AgCl>AgF

The above trend is also supported by isosteric heat of adsorption data obtained from the temperature dependence of the equilibrium isotherms. Isosteric heat of adsorption $(-\Delta H)$ values for propylene on $AgF/SiO_2$, $AgCl/SiO_2$, $AgBr/SiO_2$ and $AgI/SiO_2$ were 7.6, 8.2, 9.0, and 9.9 kcal/mol, respectively.

The π-complexation bond involves σ-donation (i.e., overlap of the 2p orbital of olefin with the 5s orbital of $Ag^+$) and d-π* backdonation (i.e., electron donation from the $4d_{yz}$ orbital of $Ag^+$ to the 2p* orbital of olefin). For anions with higher electronegativities (e.g., $F^-$), the σ-donation is stronger. However, the d-π* backdonation dominates the bonding in this case, and the backdonation follows the order shown above.

EXAMPLE 3
Substrate Effects—$AgNO_3$ Supported on $\lambda Al_2O_3$, $SiO_2$ and Zeolite In order to gain a better understanding of the behavior of π-complexation sorbents, it is necessary to also understand the effects of various substrates on olefin adsorption. This example shows the effect that the chemical and structural properties of the substrate had on adsorption behavior. To this end, several sorbents were prepared by dispersing $AgNO_3$ over three different high surface area substrates using the incipient wetness impregnation technique described previously. The substrates used were $\gamma$-$Al_2O_3$, $SiO_2$ and MCM-41 mesoporous zeolite. The MCM-41 utilized is one of a new family of mesoporous silicate molecular sieves with hexagonal arrangement of unidimensional channels with uniform sizes in the range of 20–100 Å (Kresge, et al., 1992; Beck et al., 1992). The MCM-41 utilized had a BET surface area of 1004 $m^2/g$ and an average pore size measured by the Horvath Kawazoe method to be 30 Å. The $\gamma$-$Al_2O_3$ utilized was obtained from Aleoa (PSD-350) and had a BET surface area of 340 $m^2/g$. The metal salt loading per surface area was maintained constant for each sorbent. The $AgNO_3$ loadings for $\gamma$-$Al_2O_3$, $SiO_2$, and MCM-41 were 0.16, 0.27 and 0.47 gram of salt per gram of substrate, respectively.

Figure 5:
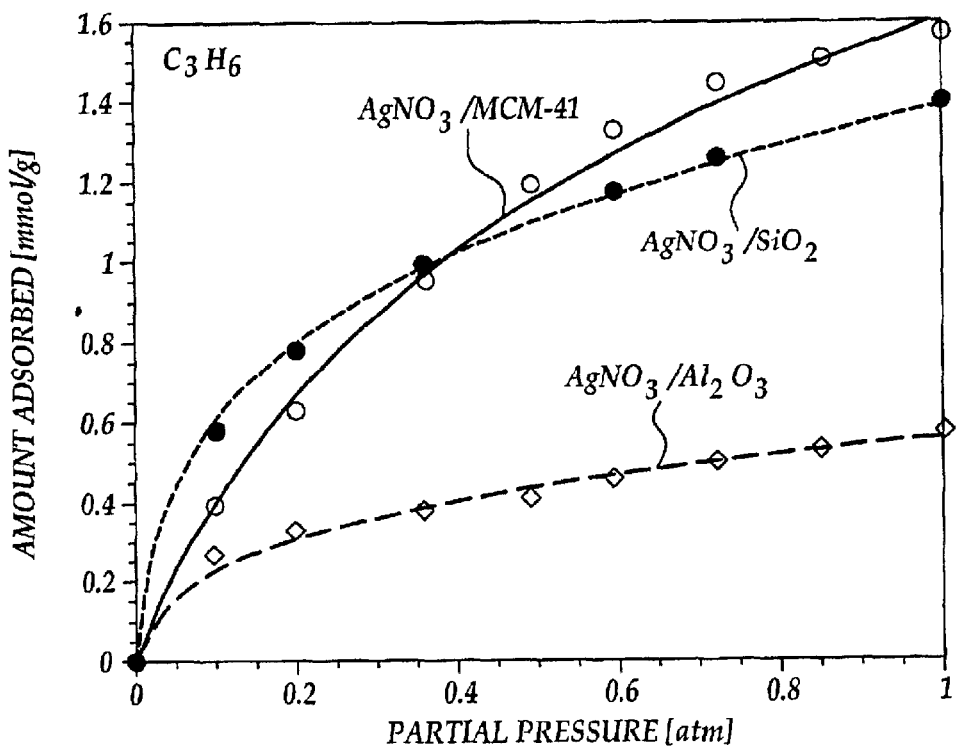
FIG. 5 shows equilibrium isotherms of $C_3H_6$ at 70° C. on incipient wetness impregnated $AgNO_3/\gamma-Al_2O_3$, $AgNO_3/SiO_2$ and $AgNO_3/MCM-41$. Lines are fitting with eq. (B).
Figure 6:
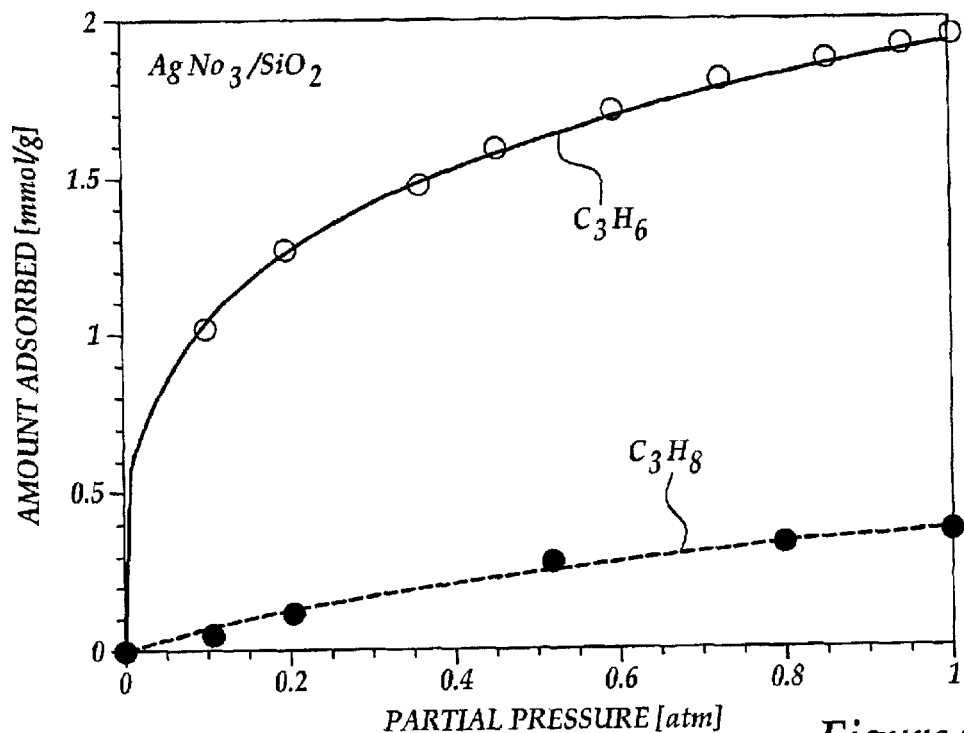
FIG. 6 shows selective adsorption of $C_3H_6$ over $C_3H_8$ at 70° C. on incipient wetness impregnated $AgNO_3/SiO_2$. Lines are fittings with eqs. (A) and (B).
Figure 7:
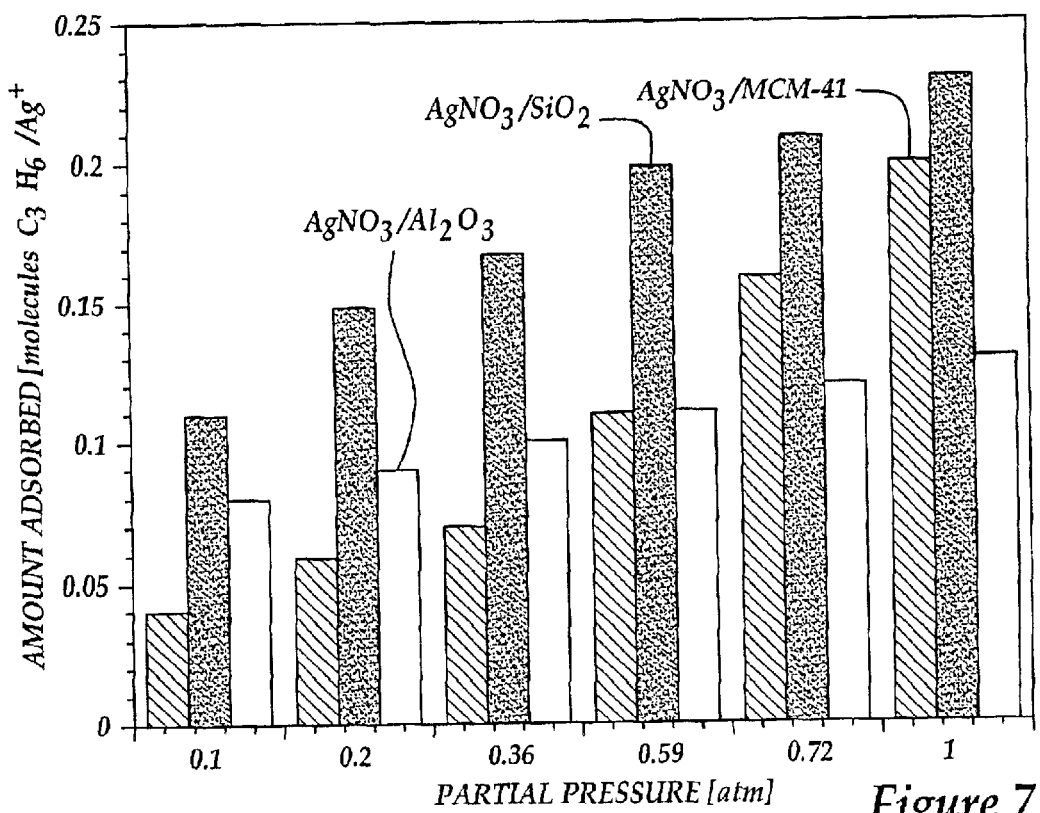
FIG. 7 shows normalized $C_3H_6$ equilibrium data at 70° C. on incipient wetness impregnated $AgNO_3/\gamma-Al_2O_3$, $AgNO_3/SiO_2$ and $AgNO_3/MCM-41$.

Equilibrium isotherms for $C_3H_6$ on wet impregnated $AgNO_3/\gamma$-$Al_2O_3$, $AgNO_3/SiO_2$ and $AgNO_3$/MCM-41 at 70° C. are shown in FIG. 5. The fitting parameters for these isotherms are shown in Table D. Adsorption capacities at 1 atm and 70° C. for $AgNO_3/\gamma Al_2O_3$, $AgNO_3/SiO_2$ and $AgNO_3$/MCM-41 were 0.48, 1.49, and 2.06 mmol/g, respectively. $C_3H_6$ adsorption on these sorbents was completely reversible. As shown in FIG. 5, all isotherms showed good working capacities which are crucial for pressure swing adsorption process (PSA). Uptake rates on all sorbents were fast with completion within 300 seconds. The overall diffusion time constants $(D/R^2)$, surface areas and average pore diameters for $AgNO_3/\gamma$-$Al_2O_3$, $AgNO_3/SiO_2$ and $AgNO_3$/MCM-41 are shown in Table E. Selective olefin over paraffin adsorption is shown in FIG. 6 for $C_3H_6$ and $C_3H_8$ at 25° C. on wet impregnated $AgNO_3/SiO_2$. The selective adsorption ratio of this sorbent at 1 atm was 6. The working capacity of a sorbent is determined by the isotherm's steepness above the knee. In order to clearly show the effect of the chemical properties of the sorbent's surface rather than the physical properties (surface area, pore size), the data was normalized to prevent bias toward the samples with higher surface areas. The normalized equilibrium data for the $C_3H_6$ adsorption at 70° C. on $AgNO_3/\gamma\text{-}Al_2O_3$, $AgNO_3/SiO_2$ and $AgNO_3/$ MCM-41 are shown in FIG. 7. Once the data had been normalized the following trend for the substrates is observed:

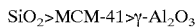

$SiO_2 > MCM\text{-}41 > \gamma\text{-}Al_2O_3$

The surfaces of $SiO_2$ and $Al_2O_3$ are both filled with oxygen atoms. Pure $SiO_2$ surface has no acidity, whereas $Al_2O_3$ has acidity due to oxide vacancies. Consequently, there are more $Ag^+$ ions that are 4-coordinated on the $SiO_2$ surface as compared to the $Al_2O_3$ surface, and there are more 5- and 6-coordinated $Ag^+$ on the $Al_2O_3$ surface. It is more favorable for the 4-coordinated $Ag^+$ ions to bond $C_2H_4$ molecules. The 5- and 6-coordinated $Ag^+$ ions are unlikely to bond olefins due to stereochemical reasons. The experimental results indeed showed that $SiO_2$ is significantly better as a substrate.

Examples 1 to 3 show new and more effective sorbents for ethane\ethylene and propane\propylene separations that were synthesized by dispersing $AgNO_3$ salt over several substrates ($\gamma\text{-}Al_2O_3$, $SiO_2$ and MCM-41) using incipient wetness impregnation technique. The capacities and selectivities of these new sorbents are significantly better than any known $\pi$-complexation sorbents. Adsorption rates for these sorbents were fast with 100% completion achieved within 300 seconds at 25° C. These characteristics make the sorbents most promising for use with pressure swing adsorption processes (PSA), which is described in the examples which follow later (Yang, 1987).

It was demonstrated that anions have significant effects on the adsorption behavior of $\pi$-complexation sorbents. It was shown that the anion effects on the selective olefin adsorption followed the trend described below:

AgI>AgBr>AgCl>AgF

This trend is opposite to the electronegativities of the anions. This was because the d-$\pi$* backdonation, rather than the $\sigma$-donation, dominated the bonding between olefin and $Ag^+$.

One of the objectives was to determine the effect various substrates have on selective olefin adsorption based on $\pi$-complexation. While the effect of the physical characteristics of a substrate such as a surface area and pore size would have on adsorption is clear, the effect of the surface chemistry properties (i.e., lyophobicity, hydrophobicity, etc.) is not well understood. The substrates selected were $\gamma\text{-}Al_2O_3$, $SiO_2$, and MCM-41. Once the data was normalized to take into account surface area, the following trend was observed:

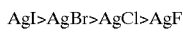

$SiO_2 > MCM\text{-}41 > \gamma\text{-}Al_2O_3$

The silica surface (on both silica gel and MCM-41) provides a better substrate due to the lack of surface oxide vacancies (unlike $\gamma\text{-}Al_2O_3$), and consequently there are more four-coordinated $Ag^+$ (which can bond olefin) and less 5- and 6-coordinated $Ag^+$ (which cannot bond olefin for steric reasons).

From the results presented in examples 1 to 3, it is clear that anions and substrate play an important role in selective olefin adsorption via $\pi$-complexation. It is possible to use these differences to manipulate the adsorptive properties of sorbents to better suit a particular application, such as PSA described below.

EXAMPLE 4

PSA Cycle Using $AgNO_3/SiO_2$ and Comparative Adsorbents

The effectiveness of these silver salt compounds was further compared to other adsorbents. Three sorbents were used in the following examples; two were commercial sorbents, (4A zeolite and carbon molecular sieve) and one was a $\pi$-complexation sorbent of the invention described above ($AgNO_3/SiO_2$). The comparison was based on modeling a PSA cycle, representative of a commercial use of such adsorbents. Equilibrium isotherms, heats of adsorption, and temperature-dependent diffusitivities were measured for four gases on three sorbents.

The 4A-type zeolite used was in powder form. The samples were degassed in vacuo ($10^{-6}$ torr) at 350° C. before each experiment. The carbon molecular sieve (CMS) utilized in this work was manufactured by Bergbau-Forschung GmbH in Germany. Unlike Type-4A zeolite, which has a discrete pore size, Bergbau-Forschung CMS has a pore-size distribution between 3 and 5 Å. The sample utilized in his work was in pellet form. The pelletized form of CMS does not affect diffusion measurements, since diffusion processes in Bergbau-Forschung CMS are controlled by intracrystalline diffusion. The CMS samples were degassed in vacuo at 90° C. before each experiment.

The $\pi$-complexation sorbent used in this work was prepared using thermal monolayer dispersion to disperse $AgNO_3$ over an $SiO_2$ substrate. The sorbent was prepared by mixing 0.32 grams of $AgNO_3$ (Stem Chemicals) per gram of $SiO_2$ (Stem Chemicals). The $SiO_2$ had a surface area of 670 $m^2/g$ and a pore volume of 0.46 $cm^3/g$. The particle size of the $SiO_2$ utilized ranged from 100 to 200 mesh. After thorough mixing, the sample was heated in air at 200° C. for 89 h to assure complete dispersion. The BET surface area of the sorbent was measured at 384 $m^2/g$ by nitrogen adsorption at 77 K. Pore size was calculated to be 23 Å using the BJH method described in detail by Barrett, et al. (1951). Other $AgNO_3/SiO_2$ ratios were also used; the ratio just given yielded the best results.

Equilibrium isotherms, uptake curves, and surface-area measurements were made utilizing a Micromeritics ASAP 2010 adsorption instrument and a Shimadzu TGA-50 thermogravimetric analyzer. The ASAP 2010 utilizes a volumetric system to obtain adsorption isotherms and uptake curves. All uptake curves were measured at a stepped pressure increment from 0 atm to 0.1 atm. Also, measurements were made at various temperatures to obtain isosteric heat of adsorption data and the temperature dependence of diffusitivities. Surface-area measurements were carried out by nitrogen adsorption at 77 K. The hydrocarbons used were: ethane (CP grade, Matheson minimum purity 99.0%), ethylene (CP grade, Matheson minimum purity 99.5%), propane (CP grade, Matheson minimum purity 99.0%), and propylene (CP grade, Matheson minimum purity 99.0%). The gases were used without further purification.

Description of the PSA Cycle

A four-step PSA cycle similar to that used by Kikkinides et al. (1993) was used in all the cases in this example. The steps involved with each cycle were as follows: (1) pressurization with the feed gas (mixture of 50% olefin and 50% paraffin on molar basis); (2) high-pressure adsorption with feed gas, that is, feedstep; (3) high-pressure cocurrent purge with part of the olefin-rich product obtained in step (4); (4)

countercurrent blowdown to a low pressure. All steps were of equal time duration.

Figure 8:
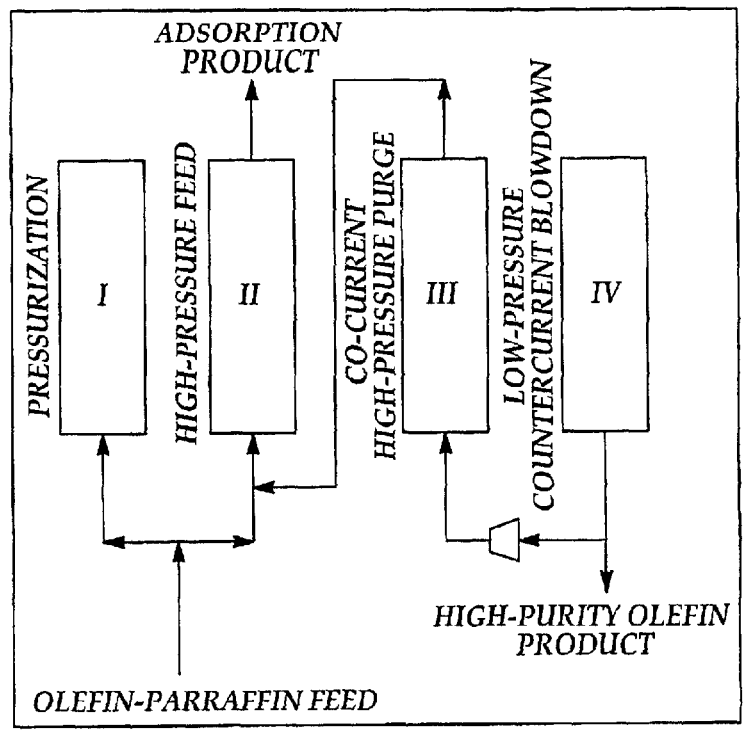
FIG. 8 shows sequence and basic steps in the four-step PSA cycle.

FIG. 8 shows the PSA cycle used. As can be seen, a portion of the high-purity olefin from the countercurrent blowdown step was compressed to the feed pressure and used for rising the bed cocurrently in step 3. Purging with the strongly adsorbed component results in a significant increase in the purity of that component in the product stream. Here, the product of the high-pressure rinse step is recycled and mixed volumetrically, with the feed gas supplied to step 2.

The objective of this example was to compare the performance of the adsorbents employing equilibrium separations, kinetic separation, and separation by exclusion of one of the components. The comparison needed to be carried out using nearly identical cycle conditions. In the case of ethane\ethylene separation, the adsorbents were compared at the same product throughput and the product purity was studied at various product recoveries. In the case of propane\propylene separation, the adsorbents had highly differing productivities, and hence the comparison was done at constant product purity and the product throughput was studied at various values of product recovery. It should be noted that the term "product" mentioned throughout this work refers to the olefin-rich product obtained in desorption step 4 unless otherwise specified. The various process variables in this work were defined as follows:

Product recovery is as defined in equation 1.

Purge-to-feed ratio (P/F) is as defined in equation 2.

Another important parameter used to gauge the adsorbent's productivity is the product throughput (also referred to as productivity in this work):

Production throughput is as per equation 3.

PSA Simulation

The model used assumes the flow of a gaseous mixture of two components in an adiabatic fixed bed packed with spherical adsorbent particles of identical size and shape. Axial dispersion for mass and heat transfer is assumed, but dispersion in the radial direction is taken to be negligible. Axial pressure drop is neglected and ideal gas law is assumed to hold since pressures involved are low. External mass-transfer limitations are assumed to be negligible. Also the gas is assumed to have constant viscosity and heat capacity.

The mass-balance equation for component k in the bed is given by the axially dispersed plug flow equation (Sun et al., 1996): See equation 4.

The overall material balance obtained is as per equation 5.

For adiabatic bed with no heat transfer with the surroundings, the overall heat balance may be written as per equation 6.

The axial dispersion coefficient ($D_{ax}$) and effective thermal conductivity ($\lambda_1$) were obtained from the mass and thermal Peclet numbers, respectively, which were obtained using standard correlations for dispersion in fixed beds (Yang, 1987).

The rate of uptake by a sorbent particle was assumed to follow the linear driving force (LDF) approximation, which holds true when $D_e t/R_p^2 > 0.1$ as per equation 7, where $q^*_k$ is the equilibrium amount adsorbed at the surface of the pellet. The LDF approximation was valid under the conditions used in this study.

Cross-term diffusivities were neglected. The effective diffusivity values ($D_{e,k}$) were assumed to be independent of the surface coverage, and they were assumed to have an exponential temperature dependence per equation 8, where $D^o_{e,k}$ was the effective diffusivity at a reference temperature $T_{ref}$.

The initial conditions of each step were the conditions at the end of the preceding step. For the first step, the bed was maintained at 0.1 atm with a certain composition of the olefin/paraffin mixture. The pressurization and the countercurrent blowdown steps were the only pressure-changing steps and the variation of pressure with time was assumed to be exponential as per equation 9, where $t_z$ was conveniently chosen time constant. The value of $t_z$ has to be chosen sufficiently small so as to obtain the desired pressure change but also sufficiently large so as to keep the (dP/dt) term in the model small enough to avoid stiffness in the numerical method used. In general, $t_z$ was 24–27% of the step time chosen.

The boundary conditions used were the Dankwerts' boundary conditions for the closed/closed vessel case as per equation 10.

Here z=0 and z=L represent the entrance and exit points in the fixed bed, respectively. The subscript m refers to the number of the step in the cycle.

For adsorption by π-complexation, the equation giving the most satisfactory fit to experimental data has been known to be the Langmuir-uniform-distribution (LUD) equation (Yang and Kikkinides, 1995; Chen and Yang, 1995). Both the physisorption and chemisorption terms were included in the isotherm. At present, however, no equation is available for its extension to multicomponent mixtures. Hence, the loading ratio correlation (LRC) extended to binary mixtures was used (Yang, 1987) as per equation 11, where $q_m$, b and n were LRC parameters. The temperature dependence of $q_m$ and b was given as per equation 12.

The coupled partial differential equations were solved using an implicit finite difference scheme employing the Crank-Nicolson method (Carnahan et al., 1969). The fixed bed was discretized into 100 spatial points and time into 200 time steps. The details of the numerical scheme used are given elsewhere (Sun et al., 1996). The PSA code was written in FORTRAN and was executed using a SUN-SPARC workstation. The model and numerical method were found to be stable and convergent for all of the runs, and all mass balances were found to be valid within 4% relative error. The machine time required for computation of one PSA cycle was about 15–20 s, and the cyclic steady state was reached in 200–500 cycles, depending upon the initial conditions used.

Results and Discussion

Isotherms and Diffusivities on 4A Zeolite

Figure 9:
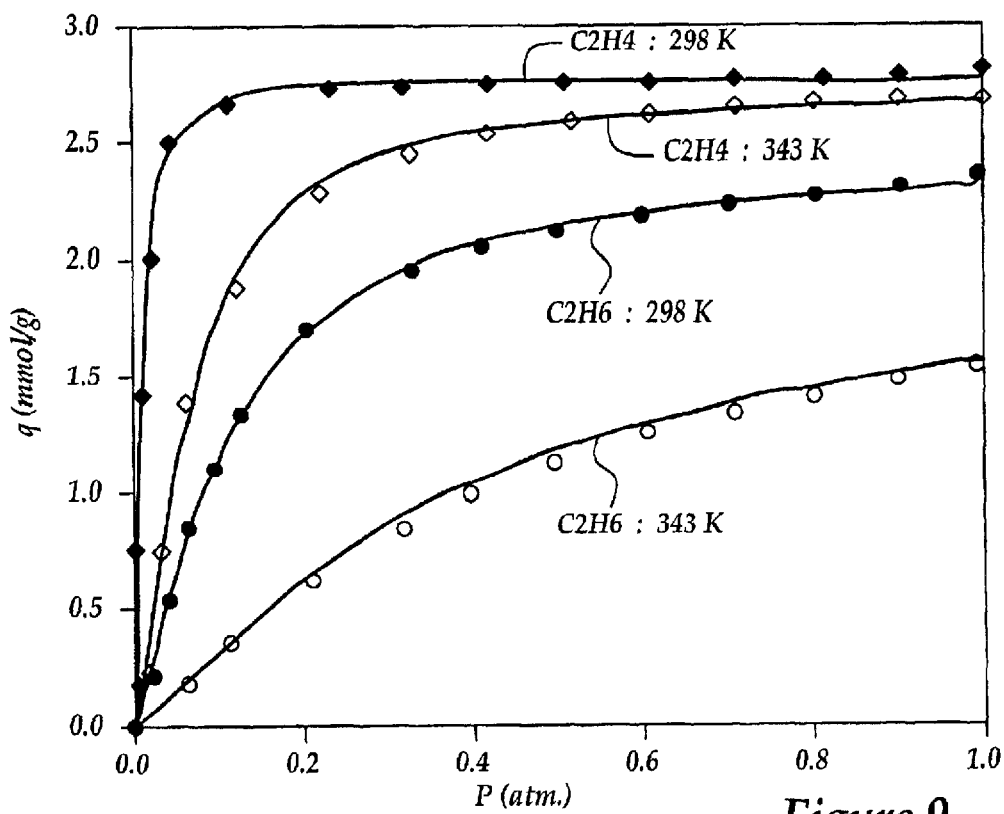
FIG. 9 shows equilibrium $C_2H_4$ and $C_2H_6$ isotherms on zeolite 4A at 25° and 70° C. For all isotherm figures, symbols are experimental data and lines are fitted isotherms.

The pure-component equilibrium isotherms of $C_2H_4$ and $C_2H_6$ on 4A zeolite at 25° C. and 70° C. are shown in FIG. 9. The equilibrium data were fitted well by the LRC model shown in Eq. 11. The fitting parameters were shown in Table 1. From FIG. 9, the amounts adsorbed at 25° C. and 1 atm for $C_2H_4$ and $C_2H_6$ were 2.8 and 2.4 mmol/g, respectively. Hence, equilibrium separation would not be feasible.

Figure 10:
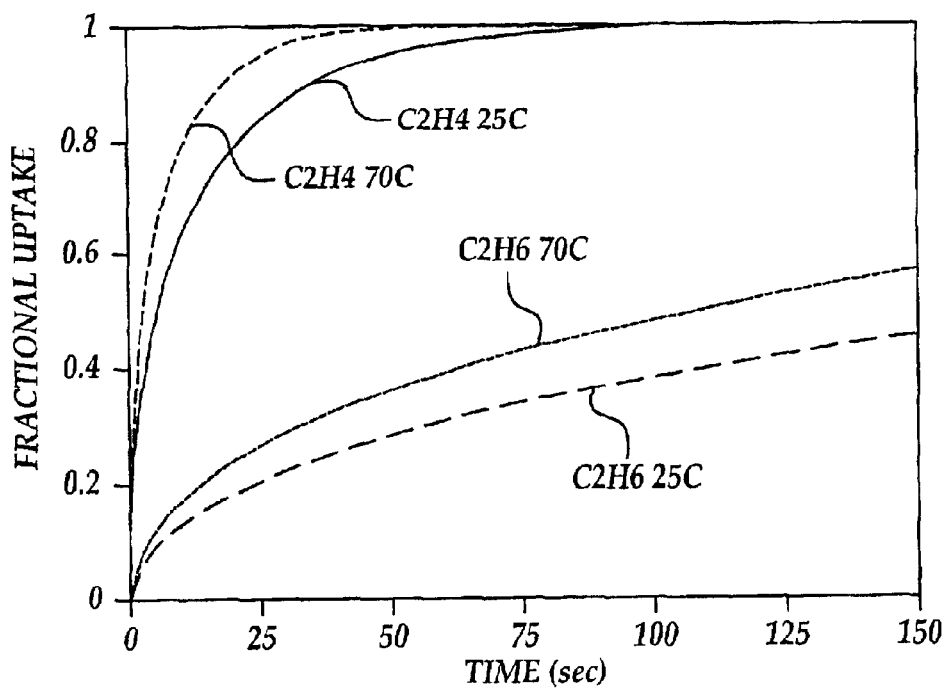
FIG. 10 shows uptake curves of $C_2H_4$ and $C_2H_6$ on zeolite 4A at 25° and 70° C. at P=0–0.1 atm.

Uptake rates were measured using Micromeritics ASAP 2010 at 25° C. and 70° C., and the results are shown in FIG. 10. The pressure increments were from 0 atm to 0.1 atm. At 25° C., after 15 s, $C_2H_4$ adsorption was approximately 75% complete, while $C_2H_6$ adsorption was only 15% complete. Diffusion time constants, $D/R^2$, were calculated by fitting experimental data with the solution for the diffusion equation for spherical particles (Kärger and Ruthven, 1992). The values of $D/R^2$ obtained for $C_2H_4$ and $C_2H_6$ at 25° C. were $5.12 \times 10^{-3}$ and $1.64 \times 10^{-4}$, L/s$^{-1}$, respectively. The ratio of these diffusivities was 31, which was similar to the ratio of pure-component diffusivities of $O_2/N_2$ in the commercial separation of air using a carbon molecular sieve. However, it was observed that the desorption rate of the $C_2H_4$ on zeolite 4A was low compared to that of adsorption rate, thus giving it an irreversible nature. Unlike $C_2H_4$, $C_2H_6$ adsorption was completely reversible at this temperature.

For purpose of simulation, however, the adsorption and desorption rates were assumed to be equal. The results of the simulation would thus represent the best separation of $C_2H_4$ and $C_2H_6$ by zeolite 4A at 25° C.

Figure 11:
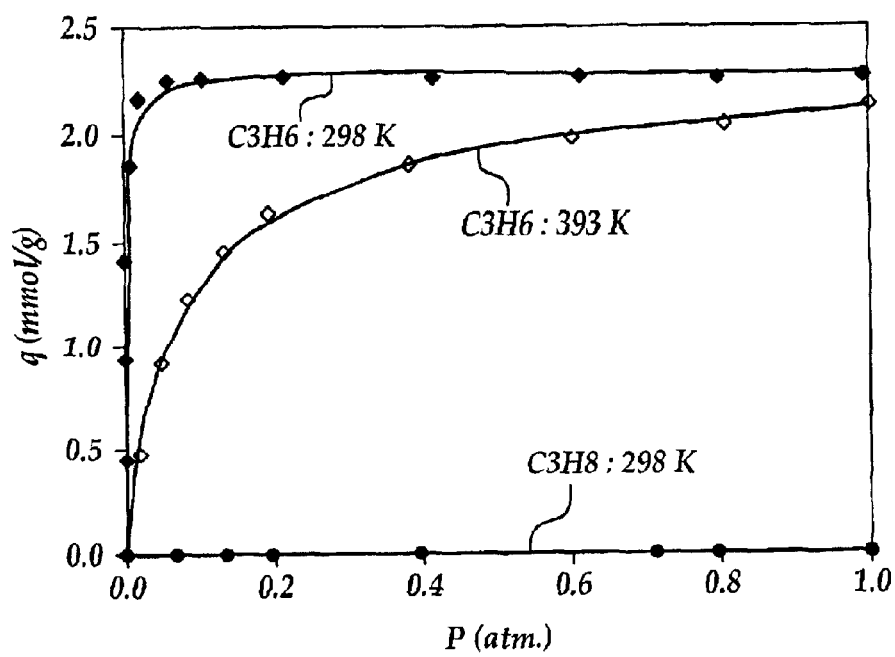
FIG. 11 shows equilibrium isotherms of $C_3H_6$ and $C_3H_8$ on zeolite 4A at 25° and 120° C.
Figure 12:
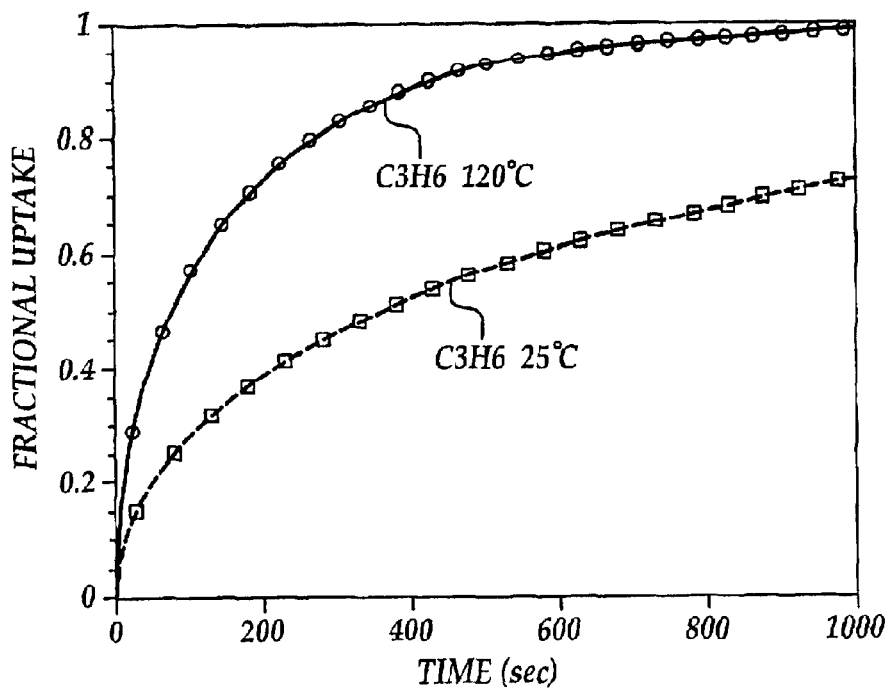
FIG. 12 shows uptake rates of $C_3H_6$ on zeolite 4A at 25° and 120° C.

Equilibrium isotherms and diffusion time constants of $C_3H_6$ and $C_3H_8$ on 4A zeolite were also measured. The isotherms are shown in FIG. 11, and the uptake rates of $C_3H_6$ are shown in FIG. 12. It is noteworthy that $C_3H_8$ was essentially excluded from the 4A zeolite, whereas the $C_3H_6$ molecule was free to diffuse. The effective aperture size of the 4A zeolite is 3.8 Å, which obviously is the demarcation between the kinetic diameters of $C_3H_6$ and $C_3H_8$. The diffusion time constants of $C_3H_6$ at 25° C. and 120° C. were $8.5 \times 10^{-5}$ $L/s^{-1}$ and $4.3 \times 10^{-4}$ $L/s^{-1}$, respectively. The temperature-dependent diffusivity values are included in Table 2. The equilibrium LRC fitting parameters are given in Table 1.

It was observed that the adsorption of $C_3H_6$ in the 4A zeolite was not completely reversible at 25° C., with approximately 10% adsorbate remaining after desorption. However, the adsorption at 120° C. was readily reversible.

Isotherms and Diffusitivities on the Carbon Molecular Sieve

Figure 13:
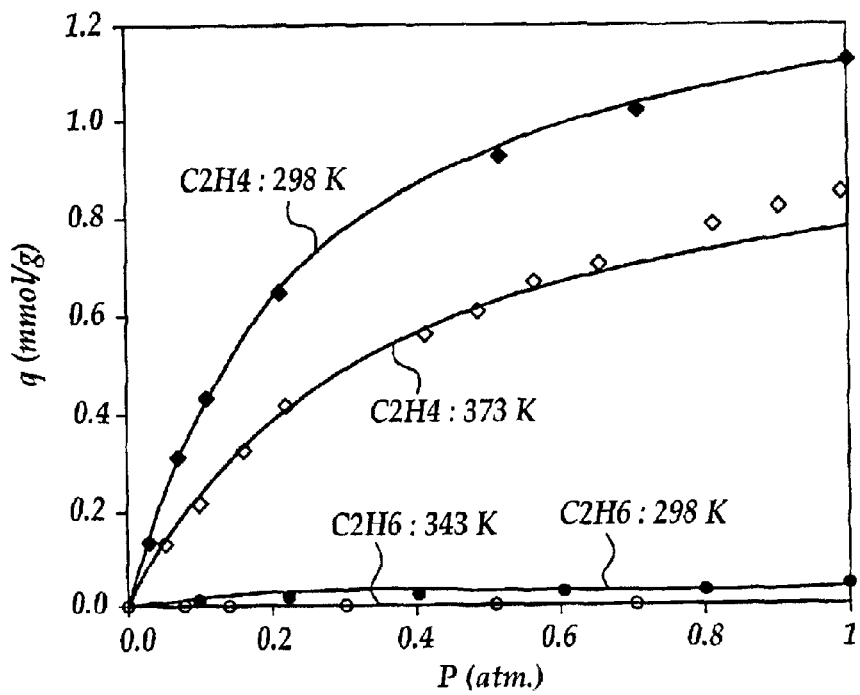
FIG. 13 shows equilibrium isotherms of $C_2H_4$ and $C_3H_6$ on molecular-sieve carbon at 25° and 100° C.

Unlike the 4A zeolite with a discrete aperture dimension, the CMS had a distribution of micropore sizes ranging from 3 Å to 5 Å. Measurements with $C_3H_6$ and $C_3H_8$ showed that these molecules were totally excluded. The equilibrium isotherms of $C_2H_4$ and $C_2H_6$ at various temperatures are shown in FIG. 13. $C_2H_6$ was nearly excluded, yet detectable amounts were observed due to the larger pores in the CMS.

The diffusion time constants for $C_2H_4$ in CMS were $1.90 \times 10^{-6}$ $L/s^{-1}$ at 25° C. and $1.77 \times 10^{-5}$ $L/s^{-1}$ at 100° C. The isotherm parameters are given in Table 1, and the temperature-dependent $D/R^2$ values are included in Table 2. Although the diffusivities were low, the equilibrium selectivity for $C_2H_4/C_2H_6$ was high. Hence, the $C_2$/CMS system was included in PSA simulation.

Equilibrium Isotherms and Diffusivities on Monolayer $AgNO_3/SiO_2$

Both $C_2H_4/C_2H_6$ and $C_3H_6/C_3H_8$ separations are effective with the $AgNO_3/SiO_2$ π-complexation sorbent, as shown in prior examples 1 to 3. Here, only $C_3H_6/C_3H_8$ was included for comparison with the other adsorbents. The Ag-resin was used for the $C_2$ separation for the purpose of evaluating separation by π-complexation. Data for $C_2H_4$ and $C_2H_6$ isotherms and diffusivity values were taken from the work by Wu et al. (1997) and are presented in Tables 1 and 2, respectively.

Figure 14:
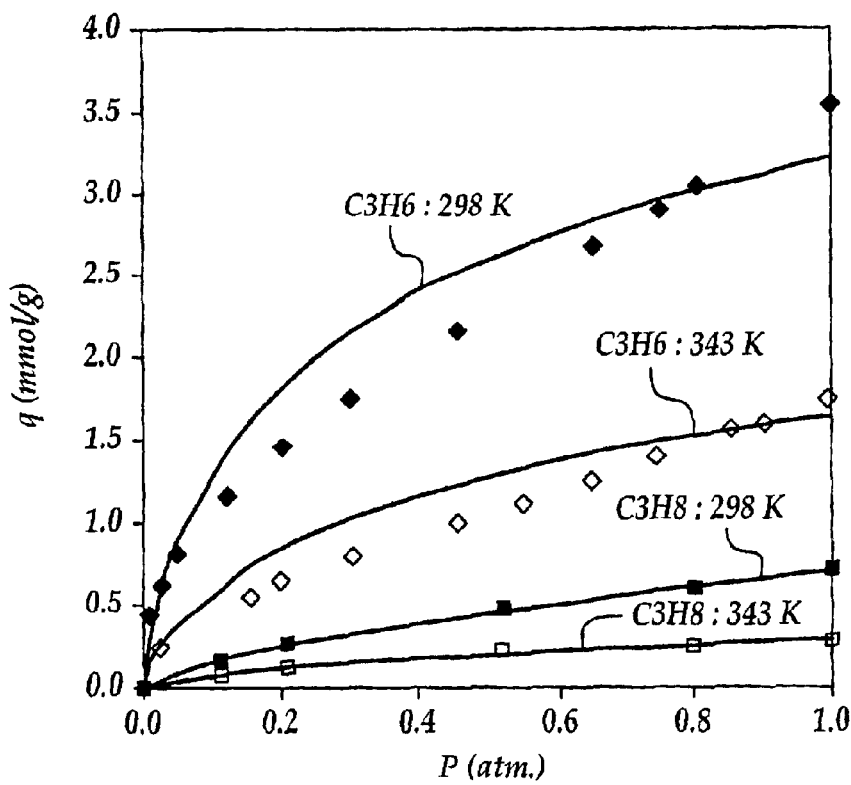
FIG. 14 shows equilibrium isotherms of $C_3H_6$ and $C_3H_8$ on monolayer $AgNO_3/SiO_2$ at 25° and 70° C.

The equilibrium isotherms of $C_3H_6$ and $C_3H_8$ and on $AgNO_3/SiO_2$ at 25° C. and 70° C. are shown in FIG. 14. The Langmuir-type isotherm (i.e, LRC) did not fit the data well due to the steepness of the equilibrium data. The best fit is shown in FIG. 14, and the fitting parameters are included in Table 1. Since the fitted isotherm undercalculated the Δq in the PSA cycle, the PSA simulation result based on the fitted isotherm would underestimate the separation.

The uptake rates were rapid and not shown here for example, the diffusion time constants for $C_3H_6$ and $C_3H_8$ at 70° C. were $1.67 \times 10^{-3}$ $L/s^{-1}$ and $1.48 \times 10^{-2}$ $L/s^{-1}$, respectively. The temperature-dependent values are included in Table 2. The rapid diffusion was due to the large pore dimensions (32 Å) in the sorbent.

Ethane/Ethylene Separation Using Comparative Adsorbents

The adsorbents that were considered for ethane/ethylene separation were zeolite 4A, Bergbau-Forschung carbon molecular sieve (CMS), and $Ag^+$-exchanged Amberlyst-35 resin. As discussed earlier, zeolite 4A had a good capacity for ethylene separation by way of kinetic separation, whereas the Bergbau-Forschung CMS had the property of excluding ethane completely. Recently, $Ag^+$-exchanged Amberlyst-35 with 36.5% degree of ion exchange (DIE) was found to have promising prospects for olefin/paraffin separation applications by virtue of steep isotherms for ethylene and comparatively flat isotherms for ethane (Wu et al., 1997).

The PSA cycle used is outlined in Table 3. In the case of zeolite 4A, a feed temperature of 25° C. was used with time for each step ranging from 80 to 480 s. As was mentioned earlier, the desorption rate of $C_2H_4$ on zeolite 4A was low compared to that of absorption at 25° C. In the present work, however, this irreversibility is neglected and equal rates of absorption and desorption are assumed, thus giving the best separation possible by this sorbent. The purge-to-feed ratio was adjusted for each cycle time so as to provide an optimum product purity and recovery.

For $Ag^+$-exchanged resin, a feed temperature of 25° C. was also employed for comparison with 4A zeolite. A study of the uptake curves for $C_2H_4$ provided by Wu et al. (1997) shows a 90% uptake after 30 min duration. Hence step times ranging from 800 s to 1,800 s were used.

Figure 15:
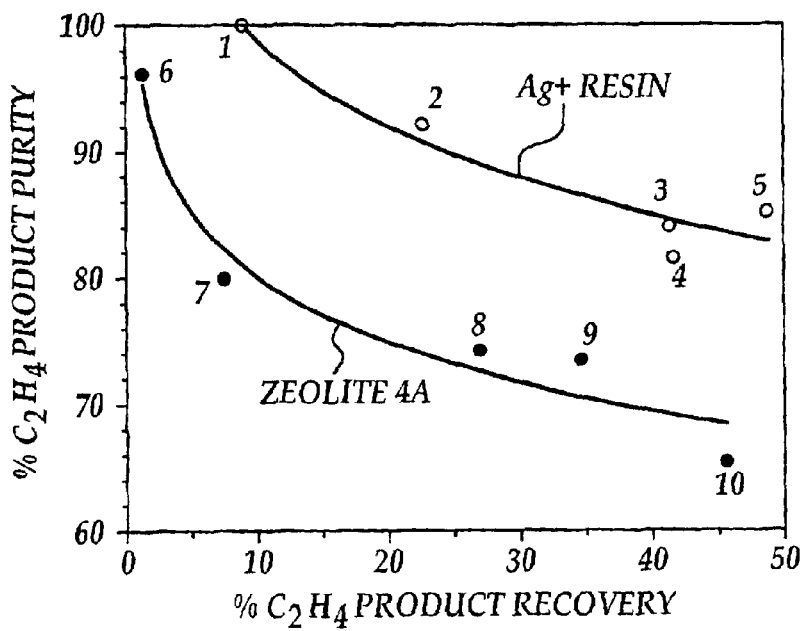
FIG. 15 shows $C_2H_4$ product purity (%) vs. $C_2H_4$ product recovery (%) for PSA using zeolite 4A and $Ag^+$-exchanged Amberlyst-35 resin at average $C_2H_4$ product throughput= $1.1 \times 10^{-4}$ kg of product/h/kg of adsorbent. Feed temperature=25° C. Inset figures refer to the number of the corresponding run shown in Table 4.

The performance of the sorbents needed to be compared by keeping one of the following three parameters constant: product purity, product recovery, and product throughput. As comparable product throughputs were obtained in the case of zeolite 4A and the $Ag^+$-Amberlyst-35, comparison was done by studying the product purity vs. product recovery at an average product throughput of about $1.1 \times 10^{-4}$ kg product/h/kg adsorbent. The PSA cycle conditions used in the simulation runs are given in Table 4 and the results of the simulations are shown in FIG. 15. The dots in the figure represent actual results of the simulation runs, while the line indicates the trend followed. As can be seen from the figure, the $C_2H_4$ product purity fell rapidly at high $C_2H_4$ product recovery for both the sorbents at constant productivity. High recovery was possible at low product purities, but it fell drastically at very high purity in the case of zeolite 4A. However, in the case of $Ag^+$-Amberlyst-35 resin sorbent, much higher $C_2H_4$ product recovery was possible compared to zeolite 4A at corresponding product purity and at the constant product throughput under consideration. Although, in general, the runs for $Ag^+$-resin show a slightly lower product throughput than that for zeolite 4A, comparison between runs 1 and 2 for $Ag^+$-resin and runs 6 and 7 for zeolite 4A in Table 4 is valid, since product throughputs are about the same for both. Hence, it can be concluded that equilibrium separation by π-complexation adsorbents such as $Ag^+$-Amberlyst-35 gives better performance than kinetic separation using zeolite 4A. Moreover, both curves in FIG. 15 could be raised by further lowering the product throughput. Although product purities in excess of 99.9% were possible for the $Ag^+$-resin at recoveries lower than 10%, the product throughput dropped further. Hence these data could not be shown in this figure. The monolayer $AgNO_3/SiO_2$ sorbent of the invention has selectivity for ethylene similar to that of $Ag^-$-resin and in addition has much higher diffusivities compared to the latter sorbent. Hence the disadvantage of having low product throughputs for $Ag^+$-resin can be overcome by using the $AgNO_3/SiO_2$ sorbent with negligible diffusion limitation.

Simulation studies were also carried out for Bergbau-Forschung CMS. It can be seen from the $C_2H_4/C_2H_6$ isotherms in FIG. 13 that $C_2H_6$ was excluded almost completely from the pores, whereas $C_2H_4$ is not. A study of the $C_2H_4$ uptake curves for CMS showed that the uptake was very slow, requiring more than 1 h to reach 80–90% of uptake for $C_2H_4$, even at a high temperature of 100° C. Simulation runs were carried out at 100° C. with a step time ranging from 4,000 to 8,000 s. Since the cycle time was high, the product throughput was very low compared to that of zeolite 4A and $Ag^+$-Amberlyst-35. Also, since the working capacity of the CMS adsorbent for $C_2H_4$ was quite small compared to that possessed by the other two adsorbents, there was a large restriction on the feed throughput and on the allowable purge-to-feed ratio. The results of PSA simulations showed that although product purities over 90% were possible, the product recoveries would not exceed 5%. The low diffusivity of the olefin caused the feed to break though the bed even at interstitial velocities as low as 0.05 m/s, thus causing considerable loss of olefin in the feed product. Even at lower product purities, the recoveries did not improve much. Further, the maximum product throughput that could be achieved was of the order of $1.4 \times 10^{-5}$ kg/h/kg sorbent, which is only 1% of that possible by zeolite 4A and $Ag^+$-resin. It was thus obvious that the performance of Bergbau-Forschung CMS as a sorbent for $C_2H_4/C_2H_6$ was very poor compared to the other sorbents despite having the property of excluding $C_2H_6$.

Several observations are evident to this point based on ethane\ethylene separation of Examples 1 to 4. The monolayer (thermally dispersed) $AgNO_3/SiO_2$ sorbent of the invention performed better than the carbon molecular sieve, the $Ag^+$ resin and the zeolite 4A. The prior examples 1–3 showed that impregnated $AgNO_3/SiO_2$ (incipient wetness) performed even better.

Propane/Propylene Separation

For the case of propane/propylene, the adsorbents that were considered for separation were zeolite 4A and monolayer $AgNO_3/SiO_2$. Zeolite 4A almost excludes propane from its pores, as can be seen from FIG. 11, and hence is an excellent prospect for $C_3H_6/C_3H_8$ separation. The $AgNO_3/SiO_2$ adsorbent of the invention possesses a good selectivity, steep isotherm, and hence a large working capacity for $C_3H_6$ compared to that for $C_3H_8$. Thus this sorbent, which employs equilibrium separation due to π-complexation, is also a good candidate for this separation. The Bergbau-Forschung CMS adsorbent was found to exclude both $C_3H_6$ and $C_3H_8$ from its pores, and hence it was not considered for this olefin/paraffin system.

The PSA cycle used for $C_3H_6/C_3H_8$ separation was identical to that used for $C_2H_4/C_2H_6$ separation discussed earlier. In the case of zeolite 4A, separation was due to the difference in diffusion rate of the two species, and hence the cycle time had to be optimized. From a study of the uptake curves shown in FIG. 12, it was decided to use step times ranging from 100 s to 800 s. As opposed to this, the $AgNO_3/SiO_2$ sorbent was found to have very fast uptake rates, and hence short step times of 60 to 400 s were used. The feed temperatures in the case of zeolite 4A and $AgNO_3/SiO_2$ were 100° C. and 70° C., respectively.

Figure 16:
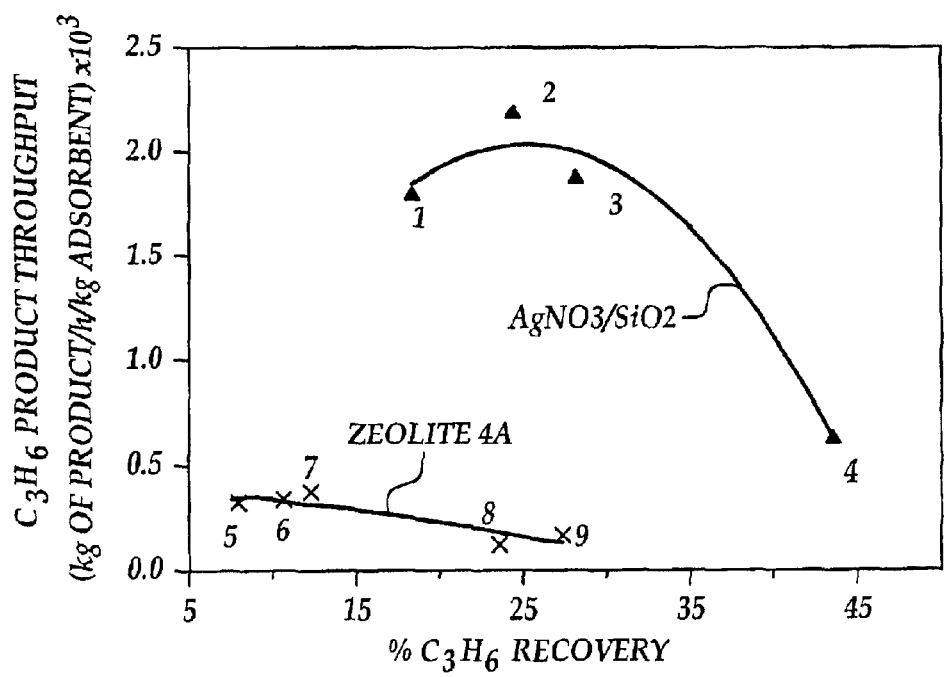
FIG. 16 shows $C_3H_6$ product throughput vs. $C_3H_6$% product recovery in this case of zeolite 4A and monolayer $AgNO_3/SiO_2$ at 99.1% $C_3H_6$ product purity. Feed temperature for zeolite 4A and $AgNO_3/SiO_2$ sorbents is 100° C. and 70° C., respectively. Inset figures refer to the number of the corresponding run shown in Table 5.

The results of the PSA simulations are shown in FIG. 16. The corresponding cycle conditions for the runs shown in the figure are summarized in Table 5. Since the product throughputs obtained for the two sorbents were quite different, the product recovery and purity could not be compared at the same product throughput, as was done in case of $C_2H_4/C_2H_6$ separation. Instead, the $C_3H_6$ product throughput of the two sorbents was compared at the same product purity of about 99%. As can be seen from FIG. 16, $AgNO_3/SiO_2$ sorbents gave almost five times the product throughput as was given by zeolite 4A It should be noted that the main purpose of this example was to compare the performance of two types of sorbent under nearly identical cycle conditions rather than provide the optimal performance of each sorbent. The product recovery can be increased by further decreasing the product throughput or decreasing the product purity. For both sorbents, product recoveries in excess of 70% were possible when product purity was lowered to 95% at product throughput of the order of $1 \times 10^{-3}$ kg of product/h/kg of adsorbent.

It was interesting to note the parabolic nature of product throughput vs. product recovery curve at constant product purity for $AgNO_3/SiO_2$. There appeared to be an optimal productivity at a particular recovery. For a PSA cycle, the aforementioned three performance variables are interrelated in a complex manner. The data points for $AgNO_3/SiO_2$ in FIG. 16 at lower recovery values were obtained at short step times, whereas those at higher recovery values were those at long step times, as can be seen in Table 4. The capacity of the sorbent was utilized to a greater extent when step time was increased. Moreover, less of the olefin was wasted as a product of the feed step, and hence recovery was seen to improve with an increase in step time. Hence, as the step time was increased from a low value, there was initially a rise in productivity as well as product recovery. However, with further increase in step time, the number of cycles performed per hour decreased, thus resulting in decrease in product throughput. In addition, as the time was increased, the less-adsorbed component, that is, $C_3H_8$, also diffused to a greater extent. This is more so for separation by $AgNO_3/SiO_2$ than by zeolite 4A because $C_3H_8$ has greater diffusivity with a higher temperature dependence than that of $C_3H_6$ for the former sorbent, as can be seen from Table 2. Hence, as per definition (Eq. 3), the product throughput decreased with higher step times, thus giving parabolic curve.

Multiplicity of Cyclic Steady States for $AgNO_3/SiO_2$

Figure 17:
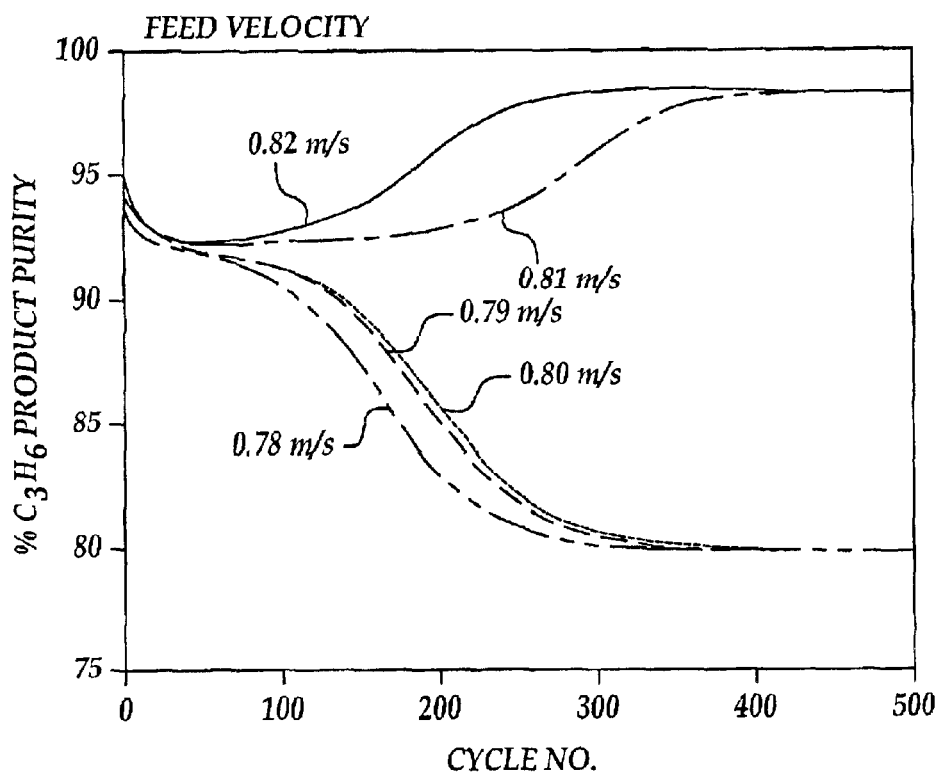
FIG. 17 shows transient behavior of $C_3H_6$ concentration in the desorption product from step 4 as system approaches cyclic steady state at different feed velocities starting from a bed saturated with 5% $C_3H_6$ and 95% $C_3H_8$ at 0.1 atm in the case of $AgNO_3/SiO_2$ sorbent. $P_H$=1.0 atm; $P_L$=0.1 atm; step time=210 s; purge velocity=0.186 cm/s; feed temperature=initial temperature=70° C.
Figure 18:
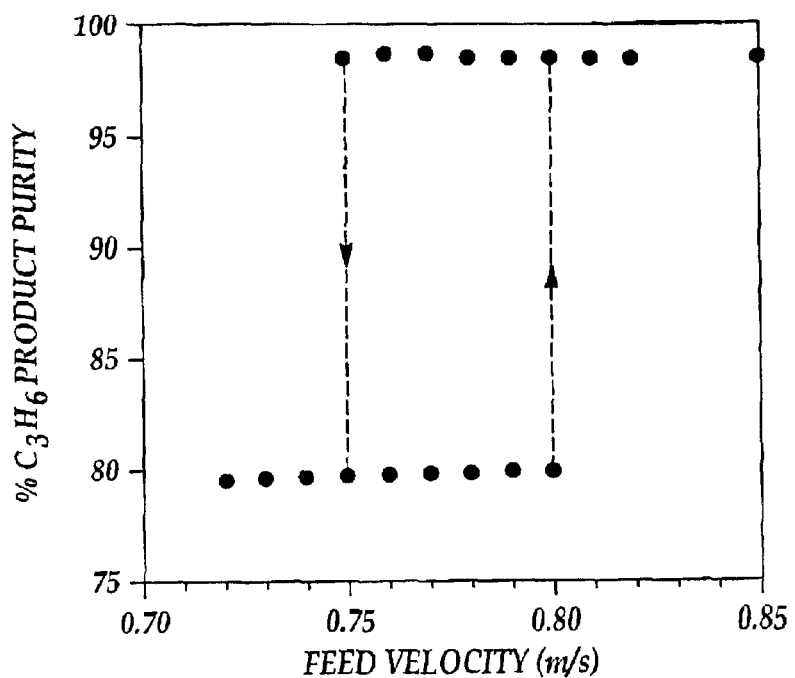
FIG. 18 shows multiplicity in PSA cyclic steady states with $AgNO_3/SiO_2$. Effect of interstitial feed velocity $U_H$, on the $C_3H_6$ concentration in the desorption (step 4) product. The lower branch started with initial temperature of 70° C., while the upper branch started with that of 120° C. $P_H$=1.0 atm; $P_L$=0.1 atm; step time 210 s; purge velocity=0.186 cm/s; feed temperature=70° C.

The transient $C_3H_6$ product purity vs. the cycle number was studied at adsorption pressure of 1 atm, desorption pressure of 0.1 atm, feed temperature of 70° C., step time of 210 s, time constant ($t_s$) of 50 s, and purge velocity of 0.186 m/s. The bed was initially saturated at 0.1 atm with a mixture of 5% $C_3H_6$ at 70° C. The variation of product purity as the system approached cyclic steady state at different feed velocities is shown in FIG. 17. A sudden jump of product purity from 80% to 98% was observed as purge velocity was increased from 0.80 m/s to 0.81 m/s. The transient product purity curves at intermediate feed velocity values showed a sigmoidal nature. It seemed as if the system tended toward an intermediate steady state (seemingly an unstable state), but then bifurcated to approach two different steady states. The product purity obtained at different feed velocities at the same purge velocity of 0.186 m/s is show in FIG. 18. All the other conditions were fixed at the values given earlier. For an initial temperature of 70° C., the product purity remained at 79.9% as feed velocity was increased from 0.72 m/s to 0.80 m/s (lower branch of FIG. 11). Thereafter, at feed velocity of 0.80 m/s and beyond, the product purity suddenly increased to 98.4%. At the same time, product recovery suddenly decreased from 41% to 28% as feed velocity was increased from 0.80 m/s to 0.81 m/s. In another set of simulations, keeping all the other parameters the same, the product purity was studied at different feed velocities with an initial temperature of 120° C. In this case, the product purity and product recovery remained at 79.9% and 41%, respectively, until feed velocity of 0.75 m/s. Beyond this value, the product purity jumped to 98.8% and the product recovery decreased to 28% (upper branch of FIG. 18). Thus, for the range of feed velocities from 0.75 m/s to 0.80 m/s, two different cyclic steady states were observed with respect to initial temperature of the PSA bed. Kikkinides et al. (1995) had seen a similar behavior of multiplicity for the system of $H_2S/CO_2/CH_4$ on 5A zeolite. In their case, multiplicity of steady states was observed with respect to different initial concentrations of the sorbates. However, in the present work, simulations carried out with different initial concentrations did not display multiplicity of periodic steady states.

Figure 19:
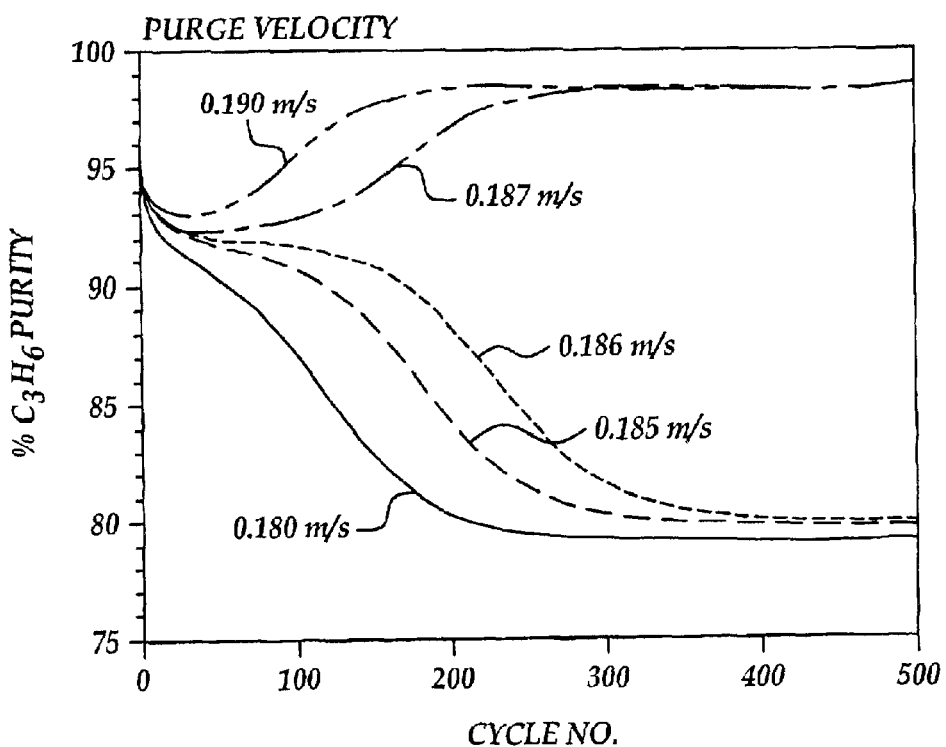
FIG. 19 shows transient behavior of $C_3H_6$ concentration in the desorption product from step 4 as system approaches cyclic steady state at different purge velocities starting from a bed saturated with 5% $C_3H_6$ and 95% $C_3H_6$ at 0.1 atm in the case of $AgNO_3/SiO_2$ sorbent. Feed temperature=initial temperature=70° C. $P_H$=1.0 atm; $P_L$=0.1 atm; step time 210 s; feed velocity=0.80 cm/s.
Figure 20:
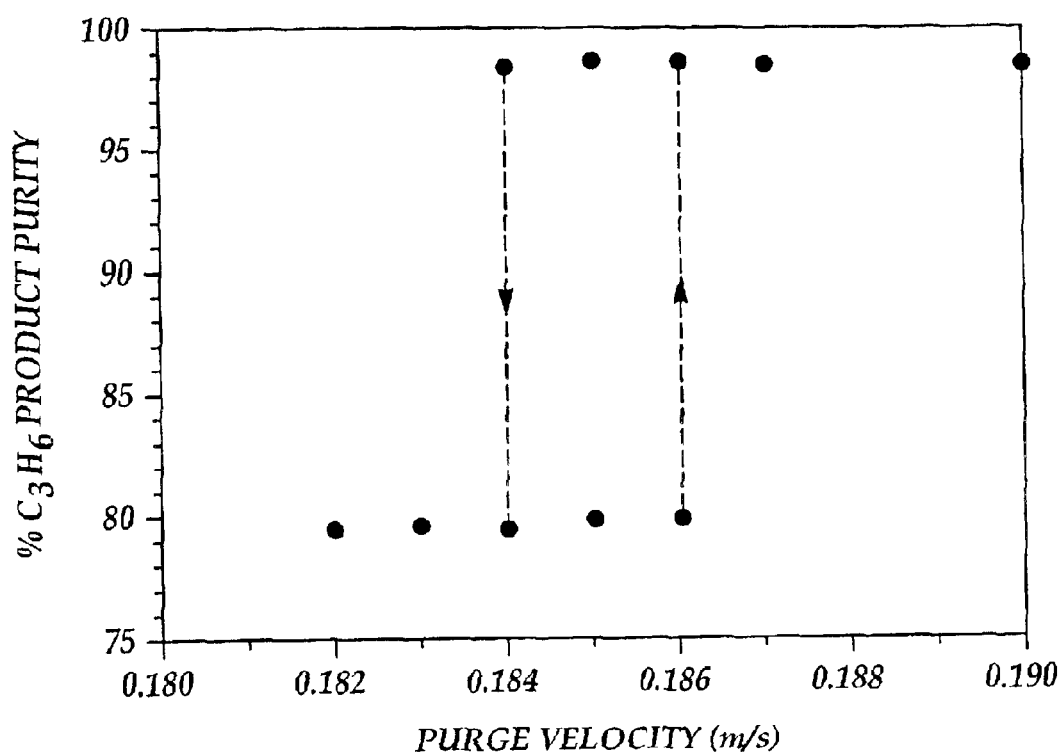
FIG. 20 shows multiplicity in PSA cyclic steady states with $AgNO_3/SiO_2$. Effect of interstitial purge velocity, Up, on the $C_3H_6$ concentration in the desorption (step 4) product. The lower branch started with initial temperature of 70° C. while the upper branch started with that of 120° C. $P_H$=atm; $P_L$=0.1 atm; step time 210 s; feed velocity=0.80 cm/s; feed temperature=70° C.

A similar type of behavior was observed with change in purge velocity. As before, when the initial temperatures of the bed were altered from 70° C. to 120° C., the system displayed multiple steady states for a range of purge velocities. FIG. 19 displays the transient product purity profiles as the system approaches cycle steady state for adsorption pressure of 1 atm, desorption pressure of 0.1 atm, feed temperature of 70° C., step of 210 s, time constant ($t_s$) of 50 s, feed velocity of 0.80 m/s, and purge velocity ranging from 0.18 m/s to 0.19 m/s. The approach to a middle unstable state and then its bifurcation to upper and lower stable steady states seen in FIG. 19 was similar to that in FIG. 17. The effect of the interstitial purge velocity on the $C_3H_6$ product concentration starting from two different initial temperatures is shown in FIG. 20. The lower branch in the figure represents the product purities obtained when the bed was started with an initial temperature of 70° C. As the purge velocity was increased from 0.186 m/s to 0.187 m/s, the product purity suddenly increased to 98.4% from 80%. The upper branch was obtained by starting with an initial temperature of 120° C., and a similar jump was seen at 0.184 m/s. Thus for the small range of purge velocities between 0.184 m/s and 0.186 m/s, multiple steady states were observed with respect to the initial temperature of the bed. A further study of the effect of initial temperature on the product-purity dependence of feed and purge velocity in the region of multiplicity revealed that all simulations carried out at initial temperatures below 106° C. followed the behavior observed for the initial temperature of 70° C., whereas all initial temperatures above 107° C. gave the behavior observed for that of 120° C.

The performance of three types of adsorbents, namely, those involving kinetic separation, exclusion of one of the components, and equilibrium separation, was compared for $C_2H_4/C_2H_6$ and $C_3H_6/C_3H_8$ systems using PSA simulations of a four-step cycle involving cocurrent purge with the strongly adsorbed species, that is, olefin. In case of the ethane/ethylene system, the performance of $AgNO_3/SiO_2$ as per prior Examples 1–3 was very attractive. Equilibrium separation using $Ag^+$-exchanged Amberlyst-35 sorbent was found to be superior compared to the kinetic separation carried out by zeolite 4A by a study of the product purity vs. recovery curve at constant product throughput. The performance of carbon molecular sieve, which was found to exclude $C_2/H_6$ from the pores, was found to be poor compared to both zeolite 4A and $Ag^+$-exchanged resin, mainly because of its slow uptake rates. The performance of $AgNO_3/SiO_2$ prepared by incipient wetness method was the most attractive for ethane/ethylene separation.

For the propane/propylene separation, equilibrium separation by monolayer $AgNO_3/SiO_2$ sorbent was found to be superior to the kinetic separation by zeolite 4A. In this case comparison was performed by comparing the product throughputs obtained using the two sorbents at a fixed $C_3H_6$ product purity of 99.1%. For $C_3H_6/C_3H_8$ separation on $AgNO_3/SiO_2$ sorbent, multiplicity of cyclic steady states was observed within certain ranges of feed and purge velocities. Within these ranges, simulation of the PSA starting from two different initial conditions while keeping the same operating conditions yielded two different stable cyclic steady states.

Spreading of monolayer $AgNO_3$ on various substrates by the incipient wetness technique is thought to be the preferred method for preparing adsorbents. The preferred $AgNO_3/SiO_2$ prepared by incipient wetness avoids decomposition of the metal compound which seems to occur with thermal dispersion heating.

TABLE A

Fitting parameters for isotherms of $C_2H_4$ (eq. 2) and $C_2H_6$ (eq. 1) at 70° C. on $SiO_2$ and $AgNO_3/SiO_2$ prepared by thermal monolayer dispersion and incipient wetness impregnation.

| | $q_{mp}$ | $q_{bp}$ | $q_{mc}$ | $b_c$ | s |
|---|---|---|---|---|---|
| $C_2H_4$ | | | | | |
| $SiO_2$ | 1.12 | 0.47 | — | — | — |
| Monolayer $AgNO_3/SiO_2$ | 0.18 | 1.78 | 1.61 | 0.20 | 7 |
| Wet impregnated $AgNO_3/SiO_2$ | 0.30 | 3.76 | 4.16 | 0.02 | 7 |
| $C_2H_6$ | | | | | |
| $SiO_2$ | 0.96 | 0.34 | — | — | — |
| Monolayer $AgNO_3/SiO_2$ | 0.18 | 1.78 | — | — | — |
| Wet impregnated $AgNO_3/SiO_2$ | 0.27 | 6.6 | — | — | — |

TABLE B

BET surface areas ($m^2/g$) for monolayer $AgX/SiO_2$ (X = F, Cl, Br, I)

| | |
|---|---|
| $AgF/SiO_2$ | 546 |
| $AgCl/SiO_2$ | 486 |
| $AgBr/SiO_2$ | 479 |
| $AgI/SiO_2$ | 405 |

TABLE C

Fitting parameters for equilibrium isotherms of $C_3H_6$ on monolayer $AgX/SiO_2$ (where X = F, Cl, Br, I) at 70° C. using eq. (2).

| | $q_{mp}$ (mmol/g) | $q_{bp}$ mmol/g | $q_{mc}$ mmol/g | $b_c$ atm$^{-1}$ | s |
|---|---|---|---|---|---|
| $AgF/SiO_2$ | 2.33 | 0.4 | 3.23 | 0.03 | 7 |
| $AgCl/SiO_2$ | 2 | 0.3 | 3.22 | 0.04 | 7 |
| $AgBr/SiO_2$ | 1.99 | 0.43 | 3.5 | 0.03 | 7 |
| $AgI/SiO_2$ | 3.1 | 0.19 | 3.8 | 0.03 | 7 |

TABLE D

Fitting parameters for $C_3H_6$ adsorption at 70° C. on $AgNO_3/Al_2O_3$, $SiO_2$, MCM-41.

| | $q_{mp}$ mmol/g | $q_{bp}$ mmol/g | $q_{mc}$ mmol/g | $b_c$ atm$^{-1}$ | s |
|---|---|---|---|---|---|
| $AgNO_3/Al_2O_3$ | 2.12 | 0.03 | 1.9 | 0.04 | 7 |
| $AgNO_3/SiO_2$ | 1.49 | 0.43 | 3.16 | 0.76 | 7 |
| $AgNO_3/MCM-41$ | 1.19 | 0.62 | 6.63 | 0.01 | 7 |

TABLE E

Diffusion time constants ($D/R^2$) for $C_3H_6$ on $AgNO_3/Al_2O_3$, $AgNO_3/SiO_2$ and $AgNO_3/MCM-41$ prepared by incipient wetness technique.

| | $D/R^2$ ($s^{-1}$) | | BET Surface Area $m^2/g$ | Pore Size Å |
|---|---|---|---|---|
| | 25° C. | 70° C. | | |
| $AgNO_3/Al_2O_3$ | $4.9 \times 10^{-3}$ | $5.8 \times 10^{-3}$ | 228 | 18 |
| $AgNO_3/SiO_2$ | $2.3 \times 10^{-3}$ | $3.5 \times 10^{-3}$ | 398 | 8 |
| $AgNO_3/MCM-41$ | $8.5 \times 10^{-3}$ | $1.4 \times 10^{-2}$ | 621 | 29 |

TABLE 1

Parameters in the Temperature-Dependent Loading Ratio Correlation Isotherms of $C_2H_4$, $C_2H_6$, $C_3H_6$ and $C_3H_8$ for Adsorbents

| Sorbent | Sorbate | $k_1$ (mmol/g) | $k_2$ (K) | $k_3$ (atm$^{-n}$) | $k_4$ (K) | n | $-\Delta H$ | $C_{pg}$ (cal./mol/K) |
|---|---|---|---|---|---|---|---|---|
| Zeolite 4A | $C_2H_4$ | 2.462 | $3.529 \times 10^{-1}$ | $1.38 \times 10^{-6}$ | 5,927 | 1.41 | 11.9 | 11.84 |
| Zeolite 4A | $C_2H_6$ | $5.956 \times 10^{-1}$ | $4.232 \times 10^2$ | $9.00 \times 10^{-5}$ | 3,599 | 1.24 | 7.15 | 14.36 |
| Zeolite 4A | $C_3H_6$ | $7.232 \times 10^{-1}$ | $3.449 \times 10^2$ | $2.81 \times 10^{-5}$ | 4,712 | 0.82 | 9.36 | 18.17 |
| Zeolite 4A | $C_3H_8$ | 2.71 | — | $4.6 \times 10^{-3}$ | — | 0.46 | — | 21.30 |
| Ag$^+$-resin | $C_2H_4$ | $2.94 \times 10^{-2}$ | $1.290 \times 10^3$ | $2.49 \times 10^{-1}$ | 632 | 0.67 | 9.35 | 11.84 |
| Ag$^+$-resin | $C_2H_6$ | $4.53 \times 10^{-4}$ | $1.829 \times 10^3$ | $2.00 \times 10^{-3}$ | 0.0 | 2.17 | 4.6 | 14.36 |
| CMS | $C_2H_4$ | 0.393 | $3.911 \times 10^2$ | $5.38 \times 10^{-1}$ | 568 | 0.98 | 3.25 | 11.84 |
| CMS | $C_2H_6$ | $1.0 \times 10^{-6}$ | 3734 | $9 \times 10^{-2}$ | 200 | 0.5 | — | 14.36 |
| AgNO$_3$/SiO$_2$ | $C_3H_6$ | $1.09 \times 10^{-1}$ | $1.169 \times 10^3$ | $9.41 \times 10^{-2}$ | 811 | 0.68 | 11.5 | 18.17 |
| AgNO$_3$/SiO$_2$ | $C_3H_8$ | $4.09 \times 10^{-1}$ | $1.743 \times 10^3$ | $2.02 \times 10^{-3}$ | 270 | 0.69 | 3.35 | 21.30 |

TABLE 2

Parameters Used in Calculating Temperature-Dependent Overall Diffusion Time Constant ($D_e/R^2$) for Diffusion of $C_2H_4$, $C_2H_6$, $C_3H_6$ and $C_3H_8$ in Adsorbents Used (Eq. 8)*

| Sorbent | Sorbate | $D^0_e/R^2$ (s$^{-1}$) | $E_{act}/R_g$ (K) |
|---|---|---|---|
| Zeolite 4A | $C_2H_4$ | $5.12 \times 10^{-3}$ | 1,477 |
| Zeolite 4A | $C_2H_6$ | $1.64 \times 10^{-4}$ | 1,231 |
| Zeolite 4A | $C_3H_6$ | $8.49 \times 10^{-5}$ | 2,051 |
| Zeolite 4A | $C_3H_8$ | — | — |
| Ag$^+$-resin | $C_2H_4$ | $1.03 \times 10^{-4}$ | 766 |
| Ag$^+$-resin | $C_2H_6$ | $1.07 \times 10^{-4}$ | 558 |
| CMS | $C_2H_4$ | $1.89 \times 10^{-6}$ | 3,438 |
| CMS | $C_2H_6$ | — | — |
| AgNO$_3$/SiO$_2$ | $C_3H_6$ | $1.43 \times 10^{-3}$ | 352 |
| AgNO$_3$/SiO$_2$ | $C_3H_8$ | $8.7 \times 10^{-3}$ | 1,206 |

*$T_{ref}$ = 298 K.

TABLE 3

Adsorption Bed Characteristics and Operating Conditions Used in the PSA Simulations

| | |
|---|---|
| Bed Length | 3.0 m |
| Diameter of adsorber bed | 1.0 m |
| Bed external porosity | 0.40 m |
| Bed density | 720 kg/m$_3$ |
| Heat capacity of bed | 0.28 cal/g/k |
| Wall temperature | 298 K (ambient) |
| Feed gas composition | 50% olefin, 50% paraffin |
| Adsorption pressure ($P_H$) | 1.0 bar |
| Desorption pressure ($P_L$) | 0.1 bar |
| Initial total pressure | 0.1 bar |
| Axial dispersion coefficient ($D_{ax}$) | $3.8 \times 10^{-2}$ m$^2$/s |
| Effective thermal conductivity ($\lambda_L$) | $2.2 \times 10^3$ W/m/K |

TABLE 4

PSA Operating Parameters for Comparison of Performances of Zeolite 4A and Ag$^+$-Exchanged Amberlyst-35 Resin for the Separation of $C_2H_4$ and $C_2H_6$*

| Run No. | Step Time (s) | Time Const. $t_3$ (s) | Interstit. Feed Vel. $U_{H\,(m/s)}$ | Interstit. Purge Vel. Up (m/s) | Desorp. Product ($C_3H_6$) % Purity | Desorp. Product $C_3H_6$ % Recovery | Desorp. Product ($C_3H_6$) Throughput (kg of Product/h/kg of Adsorbent) $\times 10^3$ |
|---|---|---|---|---|---|---|---|
| Ag$^+$ - Resin (Feed temperature = Initial temperature = 25° C. | | | | | | | |
| 1 | 1,800 | 450 | 0.40 | 0.01 | 99.73 | 8.81 | 0.135 |
| 2 | 800 | 200 | 0.15 | 0.02 | 91.92 | 22.46 | 0.062 |
| 3 | 1,200 | 300 | 0.10 | 0.05 | 83.86 | 41.12 | 0.058 |
| 4 | 1,000 | 250 | 0.10 | 0.01 | 81.26 | 41.38 | 0.061 |
| 5 | 1,380 | 345 | 0.08 | 0.01 | 85.09 | 48.73 | 0.054 |
| Zeolite 4A Sorbent (Feed temperature = Initial temperature = 25° C.) | | | | | | | |
| 6 | 80 | 15 | 1.30 | 0.15 | 96.33 | 1.32 | 0.109 |
| 7 | 480 | 120 | 0.10 | 0.03 | 79.83 | 7.18 | 0.032 |
| 8 | 80 | 15 | 0.30 | 0.10 | 73.91 | 26.71 | 0.292 |

TABLE 4-continued

PSA Operating Parameters for Comparison of Performances of Zeolite 4A and Ag$^+$-Exchanged Amberlyst-35 Resin for the Separation of C$_2$H$_4$ and C$_2$H$_6$*

| Run No. | Step Time (s) | Time Const. $t_3$ (s) | Interstit. Feed Vel. U$_{H\ (m/s)}$ | Interstit. Purge Vel. Up (m/s) | Desorp. Product (C$_3$H$_6$) % Purity | Desorp. Product C$_3$H$_6$ % Recovery | Desorp. Product (C$_3$H$_6$) Throughput (kg of Product/h/kg of Adsorbent) × 10$^3$ |
|---|---|---|---|---|---|---|---|
| 9 | 120 | 30 | 0.10 | 0.08 | 73.19 | 34.50 | 0.160 |
| 10 | 300 | 80 | 0.05 | 0.03 | 65.29 | 45.33 | 0.116 |

*P$_H$ 1.0 atm; P$_L$ = 0.1 atm

TABLE 5

PSA Operating Parameters for Comparison of Performances of Zeolite 4A and Monolayer AgNO$_3$/SiO$_2$ for the Separation of C$_3$H$_6$ and C$_3$H$_8$*

| Run No. | Step Time (s) | Time Const. $t_3$ (s) | Interstit. Feed Vel. UH (m/s) | Interstit. Purge Vel. Up (m/s) | Desorp. Product C$_3$H$_6$ % Recovery | Desorp. Product C$_3$H$_6$ % Recovery | Desorp. Product (C$_3$H$_6$) Throughput (kg of Product/h/kg of Adsorbent) 10$^3$ |
|---|---|---|---|---|---|---|---|
| AgNO$_3$/SiO$_2$ Sorbent (Feed temperature = Initial temperature = 70° C.) | | | | | | | |
| 1 | 60 | 16 | 1.40 | 0.90 | 98.57 | 18.08 | 1.79 |
| 2 | 60 | 16 | 1.40 | 0.80 | 97.60 | 24.12 | 2.19 |
| 3 | 150 | 35 | 1.00 | 0.32 | 99.03 | 27.97 | 1.87 |
| 4 | 400 | 110 | 0.20 | 0.10 | 99.05 | 43.58 | 0.65 |
| Zeolite 4A sorbent (Feed temperature = Initial temperature = 100° C. | | | | | | | |
| 5 | 100 | 30 | 0.80 | 0.13 | 99.94 | 7.95 | 0.31 |
| 6 | 400 | 110 | 0.70 | 0.05 | 99.10 | 10.54 | 0.36 |
| 7 | 400 | 110 | 0.60 | 0.05 | 99.01 | 12.16 | 0.40 |
| 8 | 800 | 240 | 0.80 | 0.045 | 99.97 | 23.59 | 0.10 |
| 9 | 600 | 150 | 0.10 | 0.065 | 99.98 | 27.29 | 0.15 |

*P$_H$ = 1.0 atm; P$_L$ = 0.1 atm $$\text{Product recovery} = \frac{(C_3H_6 \text{ from step 4}) - (C_3H_6 \text{ used for purging in step 3})}{(C_3H_6 \text{ fed in step 1 and step 2})} \quad (1)$$

$$\text{Purge-to-feed ratio}(P/F) = \frac{(C_3H_6 \text{ used to purge in step 3})}{(C_3H_6 \text{ fed in step 1 and step 2})}. \quad (2)$$

Product throughput = (3)

$$\frac{\text{Amount (kg) of } C_3H_6 \text{ produced per hour}}{\text{Amount (kg) of adsorbent}}.$$

$$\epsilon_t \frac{\partial y_k}{\partial t} - \epsilon D_{ax}\frac{\partial^2 y_k}{\partial z^2} + \epsilon \frac{\partial(uy_k)}{\partial z} + \frac{\rho_b RT}{P}\frac{\partial \overline{q_k}}{\partial t} + \frac{\epsilon_t y_k}{P}\frac{dP}{dt} = 0. \quad (4)$$

The overall material balance obtained is $$\epsilon \frac{\partial u}{\partial z} = -\frac{\rho_b RT}{P}\sum_{k=1}^{2}\frac{\overline{\partial q_k}}{\partial t} - \frac{\epsilon_t}{P}\frac{dP}{dt}. \quad (5)$$

$$\left[\epsilon\rho_g c_{pg} + \rho_b\left(c_{ps} + \sum_{k=1}^{2}\overline{q_k}c_{pg}\right)\right]\frac{\partial T}{\partial t} + \epsilon\rho_g c_{pg}u\frac{\partial T}{\partial z} - \epsilon\lambda_L\frac{\partial^2 T}{\partial z^2} = \quad (6)$$

$$\rho_b \sum_{k=1}^{2}|\Delta H_j|\frac{\partial \overline{q_k}}{\partial t} + \epsilon\frac{dP}{dt}.$$

$$\frac{\partial \overline{q_k}}{\partial t} = \frac{15D_{e,k}}{R_p^2}(q_k^* - \overline{q_k}), \quad (7)$$

$$D_{e,k} = D_{e,k}^0 \exp\left[\frac{-E_{act,k}}{R_g}\left(\frac{1}{T} - \frac{1}{T_{ref}}\right)\right], \quad (8)$$

$$P(t) = P_{fin} + (P_{ini} - P_{fin})\exp(-t/t_g), \quad (9)$$

$$D_{ax}\frac{\partial y_k}{\partial z}\bigg|_{z=0} = u_m(y_k|_{z=0} - y_{H,k}) \quad (10)$$

$$-\lambda_L\frac{\partial T}{\partial z}\bigg|_{z=0} = \rho_g c_{pg}u_m(T|_{z=0} - T_H)$$

$$\frac{\partial y_k}{\partial z}\bigg|_{z=L} = \frac{\partial T}{\partial z}\bigg|_{z=L} = 0.$$

$$q_k^* = \frac{q_{m,k}b_k P^{n_k}}{1 + \sum_{j=1}^{2}b_j P^{n_j}}, \quad (11)$$

$$q = \frac{q_{mp}b_b P}{1 + b_p P} \quad (A)$$

$$q = \frac{q_{mp}b_b P}{1 + b_p P} + \frac{q_{mc}}{2s}\ln\frac{1 + b_c P e^s}{1 + b_c P e^{-s}} \quad (B)$$

While preferred embodiments, forms and arrangements of parts of the invention have been described in detail, it will be apparent to those skilled in the art that the disclosed embodiments may be modified. Therefore, the foregoing description is to be considered exemplary rather than limiting, and the true scope of the invention is that defined in the following claims.

What is claimed is:

1. An adsorbent, comprising:

a carrier;

a silver compound supported on the carrier, said silver compound selected from the group consisting of acetate, benzoate, bromate, chlorate, perchlorate, chlorite, citrate, fluoride, nitrate, nitrite, and sulfate; said silver compound adapted to preferentially releasably retain gaseous alkenes from a gaseous mixture comprising said alkenes and at least one other compound; said silver compound present in an amount effective to releasably retain the gaseous alkenes via π-complexation bonds; said carrier being characterized by a BET surface area greater than about 50 square meters per gram and up to about 2,000 square meters per gram and comprising a plurality of pores having size greater than about 3 angstroms and up to about 10 microns; and the amount of silver compound to carrier being present in a ratio of at least 0.16:1.

2. The adsorbent of claim 1 wherein said adsorbent comprises finely divided particles of silica ($SiO_2$) with silver nitrate ($AgNO_3$) dispersed on and supported on said particles.

3. The adsorbent of claim 1 wherein said carrier is selected from the group consisting of refractory inorganic oxide, molecular sieve, and activated carbon in particle form.

4. The adsorbent of claim 3 wherein said refractory inorganic oxide is selected from the group consisting of pillared clay, alumina and silica.

5. The adsorbent of claim 3 wherein said molecular sieve is a carbon molecular sieve or a zeolite molecular sieve.

6. An adsorbent, comprising:

a carrier;

a copper salt impregnated within the carrier; the copper salt selected from the group consisting of bromide, fluoride, iodide and sulfate, said copper salt adapted to preferentially releasably retain gaseous alkenes from a gaseous mixture comprising said alkenes and at least one other compound; said copper salt present in an amount effective to releasably retain the gaseous alkenes via π-complexation bonds; and said carrier selected from the group consisting of refractory inorganic oxide, molecular sieve, and activated carbon, and characterized by a BET surface area greater than about 50 square meters per gram and up to about 2,000 square meters per gram and comprising a plurality of pores having size greater than about 3 angstroms and up to about 10 microns.

7. An adsorbent, comprising:

a carrier;

at least one of a copper compound and a silver compound supported on the carrier, the at least one of the copper compound and silver compound selected from the group consisting of acetate, benzoate, bromate, bromide, chlorate, perchlorate, chlorite, citrate, fluoride, nitrate, nitrite, sulfate, and iodide; the at least one copper compound and silver compound adapted to preferentially releasably retain gaseous alkenes from a gaseous mixture comprising said alkenes and at least one other compound at a selected temperature and pressure; the at least one of the copper compound and silver compound present in an amount effective to releasably retain the gaseous alkenes via π-complexation bonds; and the carrier being characterized by a BET surface area greater than about 50 square meters per gram and up to about 2,000 square meters per gram and comprising a plurality of pores having a size greater than the molecular diameter of the alkene.

8. The adsorbent of claim 7 wherein the at least one copper compound and silver compound is water soluble.

9. The adsorbent of claim 7 wherein said carrier is selected from the group consisting of refractory inorganic oxide, molecular sieve, and activated carbon in particle form.

10. The adsorbent of claim 9 wherein said molecular sieve is a carbon molecular sieve or a zeolite molecular sieve.

11. The adsorbent of claim 7 wherein the silver compound is silver nitrate and the carrier is silica.

12. The adsorbent of claim 7 wherein the copper compound is selected from group consisting of bromide, fluoride, iodide, and sulfate.

13. The adsorbent of claim 7 wherein the plurality of pores have a size greater than about 3 angstroms and up to about 10 microns.

14. The adsorbent of claim 7 wherein the selected temperature at which the gaseous alkenes are preferentially releasably retained ranges between about 0° C. and about 50° C. and a temperature at which the gaseous alkenes are released ranges between about 70° C. and about 200° C.

15. The adsorbent of claim 7 wherein the selected pressure at which the gaseous alkenes are preferentially releasably retained ranges between about 1 atmosphere and about 35 atmospheres.

16. The adsorbent of claim 7 wherein the gaseous alkenes are selected from a group consisting of ethylene, propylene, and mixtures thereof.

17. The adsorbent of claim 1 wherein the ratio of the silver compound to the carrier ranges between about 0.16:1 and about 0.47:1.

* * * * *